United States Patent [19]

Mudd et al.

[11] Patent Number: 4,745,186

[45] Date of Patent: May 17, 1988

[54] 2,3,4-TRIACYLHEXOSES AND MIXTURES THEREOF

[75] Inventors: John B. Mudd, Danville; Basil A. Burke, Palo Alto, both of Calif.; Jon F. Fobes, Edina, Minn.; Muraleedharan G. Nair, Dublin, Calif.

[73] Assignee: Plant Cell Research Institute, Inc., Dublin, Calif.

[21] Appl. No.: 828,108

[22] Filed: Feb. 10, 1986

Related U.S. Application Data

[63] Continuation-in-part of Ser. No. 709,550, Mar. 8, 1985, abandoned.

[51] Int. Cl.[4] ............... C07H 13/02; C07H 11/00
[52] U.S. Cl. ............... 536/119; 536/1.1; 536/115; 514/23; 514/846; 514/847; 514/783; 424/65; 424/74; 424/195.1
[58] Field of Search ............... 536/115, 119, 1.1, 18.2, 536/4.1; 514/23, 846, 847, 783; 424/65, 74, 195.1

[56] References Cited

U.S. PATENT DOCUMENTS

| | | | |
|---|---|---|---|
| 3,243,425 | 3/1966 | Whistler | 536/4.1 |
| 3,959,253 | 5/1976 | Jones | 536/18.2 |
| 4,327,183 | 4/1982 | Masuda et al. | 536/119 |
| 4,369,180 | 1/1983 | Mihalovits | 424/195.1 |
| 4,382,961 | 5/1983 | Nedeczky nee Gandy et al. | 424/195.1 |
| 4,446,131 | 5/1984 | Maughan | 424/195.1 |

OTHER PUBLICATIONS

Fobes, J. F., Mudd, J. B., and Marsden, M. P. F., "Epicuticular Lipid Accumulation on the Leaves of *Lycopersicon pennellii* (Corr.) D'Arcy and *Lycopersicon esculentum* Mill.", Plant Physiol. (Apr. 1985), 77: 567–570.

Primary Examiner—Ronald W. Griffin
Attorney, Agent, or Firm—Ciotti & Murashige, Irell & Manella

[57] ABSTRACT

The present invention comprises a new class of 2,3,4-tri-O-acylhexoses and mixtures thereof. Members of the new class of compounds are comprised of a hexose sugar having fatty acids attached at the 2, 3 and 4 positions of the hexose moiety. The fatty acids can be saturated or unsaturated, and can have a relative molecular size of up to $C_{30}$. When at least one of the acylating fatty acid groups on the hexose molecule contains more than 7 carbons, the resulting 2,3,4-tri-O-acylhexoses (or mixtures thereof) have a non-bitter taste. On the other hand, when none of the acylating fatty acids have more than 7 carbons, the resulting 2,3,4-tri-O-acylhexoses (and mixtures that contain them) are bitter when tasted.

The new 2,3,4-tri-O-acylhexoses can be synthesized using known chemical methods. Alternatively, the new compounds, and especially mixtures thereof, are obtained as the result of selective extraction and purification of the epicuticular exudate from *Lycopersicon pennellii* plant parts. Mixtures of 2,3,4-tri-O-acylhexoses, especially as found in the *Lycopersicon pennellii* natural plant extract, or the glucolipid fraction thereof, are useful as evaporation suppressants, antitranspirants and antidesiccants. The *Lycopersicon pennellii* natural plant extract is also useful as an ingredient in cosmetic and toiletry formulations, while the non-bitter glucolipid subfraction is especially useful as a "low calorie" substitute for fats in foods.

35 Claims, 2 Drawing Sheets

Figure 1. Synthesis of 2,3,4-tri-O-isobutanoylglucose.
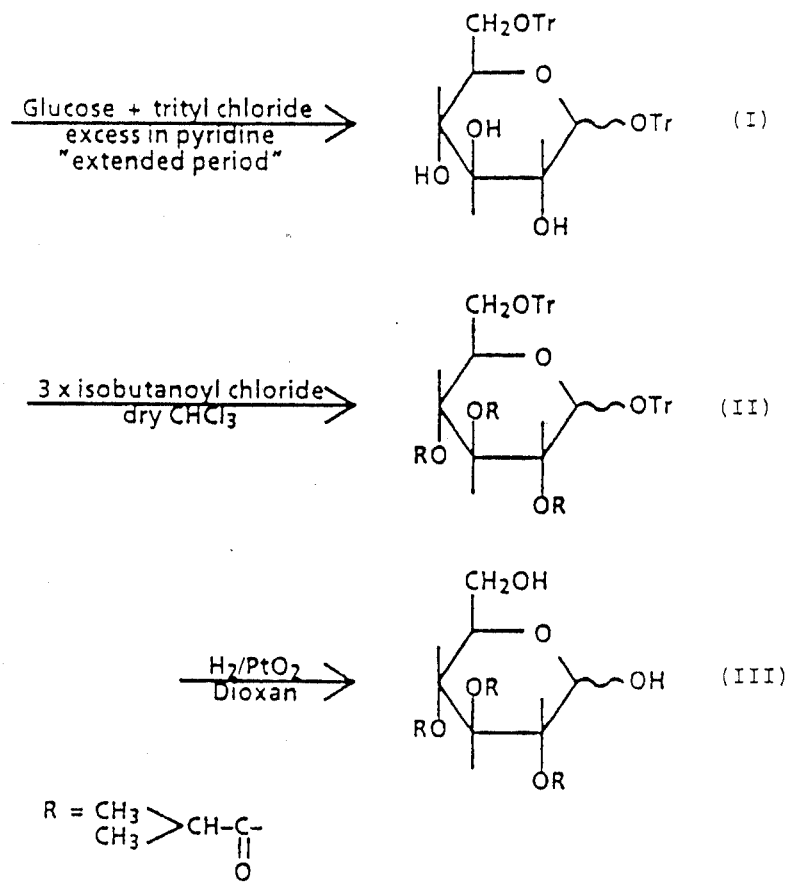

Figure 2. Synthesis of the 1-O methyl derivative of the glucolipids.
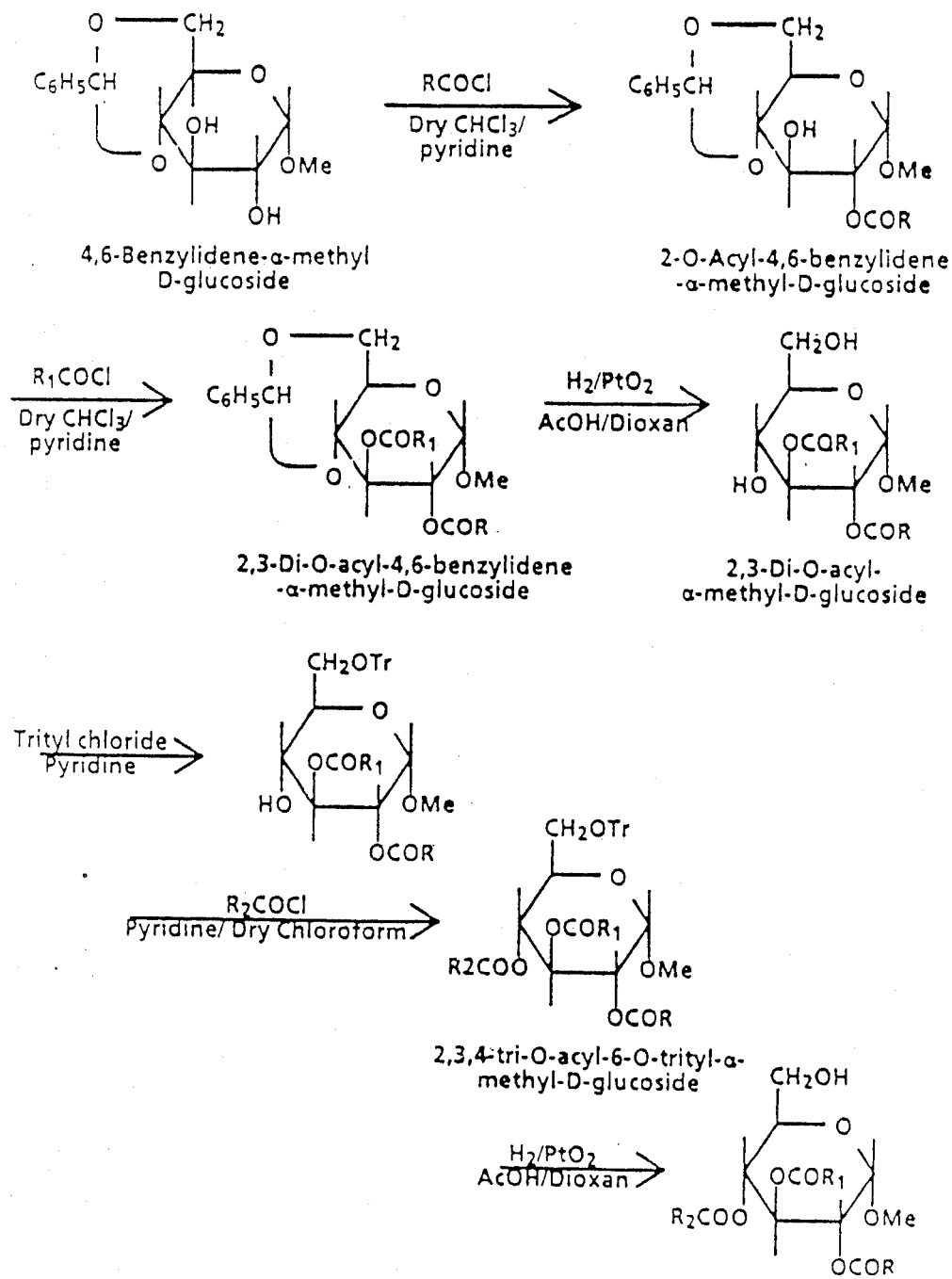

2,3,4-TRIACYLHEXOSES AND MIXTURES THEREOF

CROSS REFERENCE TO RELATED APPLICATION

This application is a continuation-in-part of U.S. Ser. No. 709,550, filed Mar. 8, 1985, now abandoned.

FIELD OF THE INVENTION

This invention relates to 2,3,4-tri-O-acylhexopyranoses referred to herein as 2,3,4-tri-O-acylhexoses. This invention also relates to 2,3,4-tri-O-acylhexoses that are classified according to taste as being either bitter or non-bitter. In addition, the present invention relates to mixtures of 2,3,4-tri-O-acylhexoses. The compositions are preferably derived as the result of selective extraction and purification of the epicuticular exudate from *Lycopersicon pennellii* plant parts. The compositions are useful in new cosmetic and toiletry formulations for external use, as "low calorie" fat substitutes in food, and as evaporation suppressants, antitranspirants and antidesiccants. Non-bitter tasting 2,3,4-tri-O-acylhexoses are especially useful as low calorie fat substitutes in foods and as an ingredient in cosmetic and toiletry formulations such as lipsticks. Mixtures of bitter tasting 2,3,4-tri-O-acylhexoses are useful in cosmetic and toiletry formulations where the bitter taste does not matter, or where the bitter taste can be used to discourage ingestion of the cosmetic or toiletry product by babies or small children.

BACKGROUND OF THE INVENTION

The plant species *Lycopersicon pennellii* Corr. (also known as *Solanum pennellii* Corr.) is known to inhabit the extremely dry, lower, western slopes of the Central Peruvian Andes. This species has a rather wide geographic distribution that extends from El Horador (Depto. Piura) in northern Peru to Camana (Depto. Arequipa) in southern Peru. The autecology of these native populations is such that often the only other vegetation growing in close proximity to *Lycopersicon pennellii* plants are cacti and bromeliads.

As a plant species, *Lycopersicon pennellii* is morphologically intermediate between potato and tomato. However, since *Lycopersicon pennellii* is interfertile in controlled pollinations with the cultivated tomato, it is commonly grouped with other wild species of tomato. Yu (1972) and Rick (1973) have shown that among tomato species, *Lycopersicon pennellii* leaves have a unique and special ability to withstand desiccation. They also point out that *Lycopersicon* pennellii distinguishes itself from other *Lycopersicon* species, except *Lycopersicon chilense*, in its ability to withstand conditions of extreme drought.

Both native, greenhouse and field populations of *Lycopersicon pennellii* have oily glands that produce a sticky exudate which covers the surfaces of *Lycopersicon pennellii* leaves, stems, peduncles, calyxes and fruits. An analysis of lipids in the leaves of *Lycopersicon pennellii* by Ermakov (1980) shows that the leaves have a high lipid content. The Ermakov study further shows that the *Lycopersicon pennellii* leaf lipids contain some 15 fatty acid components, the predominant ones being saturated fatty acids, especially capric acid (C10:0). In cultivated tomato leaves, e.g., the cultivar Gruntovy Gribovsky, Ermakov states that unsaturated fatty acids, especially linolenic acid (C18:3), usually prevail.

In addition to analyzing total leaf lipids, Ermakov also analyzed lipids isolated from the glandular hairs of *Lycopersicon pennelli* leaves. His results show that the glandular hair lipids are mainly polar and that they comprise over 70 percent of the total lipids in the leaves. In comparing the glandular hair lipids with well known plant galactolipids (for which a high concentration of unsaturated fatty acids is characteristic), Ermakov points out the glandular hair lipids have a high concentration of saturated fatty acids, especially those with a relative molecular size or length of up to C14.

REFERENCE LIST

The scientific publications cited herein are listed below; each is expressly incorporated by reference.

1. D'Arcy, W. G. (1982) "Combinations in *Lycopersicon* (Solaneceau)", *Phytologia* 51:240.
2. Draize, J. H., "Dermal Toxicity", Appraisal of the Safety of Chemicals in Foods, Drugs and Cosmetics, (The Association of Food and Drug Officials of the United States), 1975(a), page 47.
3. Draize, J. H., ibid., 1975(b), pages 49–51.
4. Ermakov, E. L. (1980), "Features of the chemical composition of the leaf lipids in *Solanum pennellii* Corr.", *Byull Vses Nauchno-Issled Inst Rastenievod im N.I. Vavilova* 105:72–77.
5. Flick, E. W., *Cosmetic and Toiletry Formulations*, Noyes Publications, Park Ridge, N.J., 1984.
6. Fobes, J. F., Mudd, J. B., and Marsden, M. P. F., "Epicuticular Lipid Accumulation on the Leaves of *Lycopersicon pennellii* (Corr.) D'Arcy and *Lycopersicon esculentum* Mill", *Plant Physiol,* (April 1985) 77: 567–570.
7. Fox, C., "Skin Care: An Overview and Update on the State of the Art and Science", *Cosmetics & Toiletries,* 99:41–54, March, 1984.
8. Rick, C. M. (1973) "Potential genetic resources in tomato species: Clues from observation in native habitats", In AM Srb, ed., *Handbook of Genetics,* Vol. 2. Plenum Press, N.Y., pp. 255–269.
9. Sagarin, E., (editor), *Cosmetics Science and Technology,* Interscience Publishers, Inc., N.Y., 1957.
10. Strianese, S. J., "Hand Creams and Lotions" in *Cosmetics Science and Technology, (edited by Edward Sagarin),* Interscience Publishers, Inc., N.Y., 1957, pages 147–181.
11. Yu, A. T. T. (1972), "The genetics and physiology of water usage in *Solanum pennellii* Corr. and its hybrids with *Lycopersicon esculentum* Mill", Ph.D. Thesis, Univ. Calif, Davis.

DEFINITIONS

In the present specification and claims, reference will be made to phrases and terms of art which are expressly defined for use herein as follows:

The present invention comprises a new class of 2,3,4-tri-O-acylhexoses, mixtures thereof, and uses therefor. As used herein to describe members of the new class of 2,3,4-tri-O-acylhexoses, the term hexose includes most carbon sugars, particularly glucose, mannose, galactose, and also including allose, altrose, gulose, idose, and talose. As used herein such hexoses include both the D forms commonly found in nature as well as the L-hexoses that can be produced synthetically, and mixtures thereof.

As used herein, *Lycopersicon pennellii* "epicuticular lipids" mean those lipids or lipid-like compounds, including glycolipids, extracted from *Lycopersicon pennellii* plant parts as the result of briefly exposing the *Lycopersicon pennellii* plant parts to organic solvent.

As used herein, "selective extraction and purification of *Lycopersicon pennellii* plant parts" means brief exposure of *Lycopersicon pennellii* plant parts (especially leaves and stems) to organic solvent, followed by recovery and purification of the plant products extracted thereby. Examples of some specific methods for accomplishing this selective extraction and purification of the *Lycopersicon pennellii* plant parts are disclosed below under the heading "Methods for Making 2,3,4-Tri-O-acylhexoses and Mixtures Thereof".

As used herein, when referring to the amount of time *Lycopersicon pennellii* plant parts are exposed to organic solvent, the word "briefly" means the amount of time sufficient to extract the *Lycopersicon pennellii* epicuticular lipids without also extracting other plant substances, such as intracellular lipids, found deeper within the plant. What constitutes a sufficient time to extract the *Lycopersicon pennellii* epicuticular lipids without also extracting contaminating substances will vary according to the extraction solvent and process being used, but can be determined without undue experimentation by those skilled in the art. A sufficient time will often range from about 10 seconds to about 10 minutes. As disclosed below under the heading "Methods for Making 2,3,4-Tri-O-acylhexoses and Mixtures Thereof", when *Lycopersicon pennellii* leaves were extracted with chloroform (1:10, wet weight of leaf tissue: weight of solvent), the extraction time was about one minute.

The terms "total extract", "(TE)", "epicuticular exudate fraction", and "epicuticular exudate extract" are synonymous and equivalent terms used to denote the *Lycopersicon pennellii* extraction product mixture remaining after *Lycopersicon pennellii* plant parts are briefly exposed to organic solvent, and then the solvent is removed therefrom.

As used herein, "glycolipid" is a generic term referring to hexose sugars acylated with fatty acids; "glucolipid" is a more specific term that refers to glucose as the sugar acylated with fatty acids. The generic term "glycolipid" includes the more specific term "glucolipid".

When used herein to refer to *Lycopersicon pennellii* extraction products, the terms "glycolipid fraction", "glucolipid fraction", "G fraction" and "(G)" are synonymous and equivalent terms used to denote the extraction product obtained when the *Lycopersicon pennellii* "total extract" is further purified to remove all or some non-glycolipid components (alkanes, terpenes, pigments, etc.).

As used herein, the term "*Lycopersicon pennellii* natural plant extract" expressly denotes, comprises and includes either the *Lycopersicon pennellii* "total extract" (TE), also referred to herein as the "epicuticular exudate fraction" or "epicuticular exudate extract", or the "G fraction" (G), also referred to herein as "glycolipid fraction" or "glucolipid fraction", thereof.

As used herein, "NBG" means non-bitter glucolipid. "BG" means bitter glucolipid. According to the method disclosed herein, the *Lycopersicon pennellii* glucolipid (G) fraction can be further separated into bitter (BG) and non-bitter (NBG) subfractions. BG subfractions are characterized by a bitter taste and the presence of glucolipids having no more than 7 carbons in any acylating fatty acid groups on the glucose molecule. NBG subfractions are characterized by a non-bitter taste, by the presence of glucolipids having more than 7 carbons in at least one of the acylating fatty acid groups on the glucose molecule, and by the substantial absence of taste effective BG components.

As used herein, cosmetic and toiletry compositions include but are not limited to creams, lotions, shampoos, soaps, lipsticks, eye creams, milks, rouges, make-ups, foundations, deodorants, antiperspirants, conditioners, hair grooming products, shaving products, sun care products, bath products, and the like.

As used herein, standard cosmetic and toiletry ingredients means ingredients used by those skilled in the cosmetic and toiletry arts to make standard cosmetic and toiletry compositions. Such standard ingredients include, but are not limited, to fragrances, pigments, preservatives, antioxidants, stabilizers, solubilizers, emollients, barrier agents, healing agents, humectants, emulsifiers, and the like, plus compounds on a list of standard cosmetic and toiletry ingredients provided by Fox ("Skin Care: An Overview and Update on the State of the Art and Science", Cosmetic & Toiletries, Volume 99, March, 1984 at pages 46–52).

As used herein, the term "fat" includes "oils".

As used herein, "food formulations" include but are not limited to food compositions such as breads, cakes, candies, cookies, frostings, gravies, ice creams, margarines, mayonnaises, meat fillings, pates, pie crusts, pie fillings, puddings, sauces, soups, spreads, vegetable fillings and the like.

As used herein, the phrase "suitable standard food ingredients" mean foods and/or flavorings or combinations of foods and/or flavorings used by those skilled in the food arts to make standard food formulations. Such standard ingredients include but are not limited to baking powders and sodas, bouillons, breads, cheeses, chocolates, coconuts, colorings, creams, eggs, fats, flours, flavorings, fruits, gelatins, herbs, lards, meats, milks, nuts, oils, preservatives, proteins, spices, stabilizers, stocks, sugars, vegetables, vinegars, vitamins, and the like.

As used herein, when the term "low calorie" is used in conjunction with the *Lycopersicon pennellii* AG fraction or foods that contain the G fraction, the term "low calorie" means having fewer metabolizable fatty acids and therefore fewer available calories.

BRIEF DESCRIPTION OF THE FIGURES

FIG. 1 is a chemical flow chart illustrating synthesis of 2,3,4-tri-O-acylhexoses of the present invention, wherein the acylating groups are identical, by outlining synthesis of 2,3,4-tri-O-isobutanoyl-glucose.

FIG. 2 is a chemical flow chart illustrating synthesis of 2,3,4-tri-O-acylhexoses of the present invention, wherein the acylating groups are mixed, by outlining synthesis of mixed 2,3,4-tri-O-acyl-alpha-methyl-D-glucoside.

SUMMARY OF THE INVENTION

One embodiment of the present invention comprises a new class of 2,3,4-tri-O-acyl D- and/or L-hexoses having the structure I:

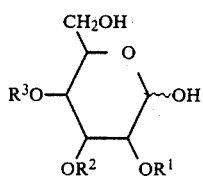

Structure I wherein
the hexose is a hexose selected from the group composed of glucose, mannose, galactose, allose, altrose, gulose, idose, and talose, (preferably glucose),
the anomeric (C-1) substituent is either alpha or beta, and
$R^1$, $R^2$, and $R^3$ are acyl groups of fatty acids independently selected from the group comprised of normal-, iso-, and anteiso- alkanoic and alkenoic acids containing about three to about thirty (preferably about four to about twenty) carbons.

In a preferred form, $R^1$, $R^2$, and $R^3$ are acyl groups of fatty acids independently selected from the group comprised of 2-methylpropanoic acid (isobutyric acid), 3-methylbutanoic acid, 2-methylbutanoic acid, 8-methylnonanoic acid and n-decanoic acid.

Mixtures of 2,3,4-tri-O-acylhexoses, in varying proportions, may be preferably derived as the result of selective extraction and purification of the epicuticular exudate from *Lycopersicon pennellii* plant parts. A typical total extract (TE) mixture is comprised of approximately 89%–95% glycolipids, approximately 5%–10% alkanes and approximately 1% terpenoids. A typical distribution of fatty acid components in a glucolipid (G) mixture (comprised essentially of hexose sugar components and fatty acid components, wherein the hexose sugar components of the mixture are glucose molecules) is about 41% 2-methylpropanoic acid, about 4.5% 2-methylbutanoic acid, about 4% 3-methylbutanoic acid, about 31.5% 8-methylnonanoic acid, and about 10.5% decanoic acid. At room temperature this purified "glucolipid mixture" is a colorless, odorless, oily liquid.

DETAILED DESCRIPTION OF THE INVENTION

The 2,3,4-tri-O-acylhexoses of this invention, some members of which can preferably be obtained by selective extraction and purification of the epicuticular exudate from *Lycopersicon pennellii* plant parts is especially surprising. In nature, when a hexose is bound to a lipid, such binding is usually through the 1 hydroxyl of the hexose molecule. In vitro, during chemical synthesis, unprotected hexose derivatives tend to have the 1 and 6 positions substituted before the 2, 3 or 4 position carbons are substituted. This is because of the greater activities of the 1 and 6 hydroxyls.

The G fraction is characterized by a bitter taste. In a distinct embodiment of this invention, it has been discovered that the bitterness may be removed from G fraction by separating a BG subfraction and recovering a non-bitter, NBG subfraction. Thus, another embodiment of the present invention comprises a new class of triacyl D- and/or L- hexoses having the structure I wherein at least one of $R_1$, $R_2$ or $R_3$ contains more than 7 carbons, preferably about 10 to about 30 carbons, more preferably about 10 to about 18 carbons.

While compositions of the present invention may be prepared synthetically, it is presently preferred to isolate them from *Lycopersicon pennellii* plant parts by extraction with an organic solvent. Impurities in the extract such as alkanes, terpenes and pigments, may be removed from the extract by various means as will be apparent to one of ordinary skill in the art. Similarly, separation of bitter and non-bitter subfractions may be accomplished by various means as will be apparent to one of ordinary skill in the art.

A preferred method for separating the *Lycopersicon pennellii* glycolipid fraction into bitter and non-bitter subfractions is based on their relative solubilities in aqueous methanol and hexane. According to the method the *Lycopersicon pennellii* alkane-free exudate is dissolved in methanol. The resulting glucolipid/methanol solution is then mixed with water to achieve a 4:1 methanol to water ratio. This resulting mixture is then extracted with hexane. The aqueous-methanol solution remaining after the hexane extraction is then diluted with water (to get a 2:1 methanol-water ratio) and extracted at least twice with hexane. This results in a "hexane phase" and an "aqueous-methanol phase". The more polar "bitter" 2,3,4-tri-O-acylglucoses are more soluble in aqueous methanol than are the less polar non-bitter 2,3,4-tri-O-acylglucoses. Thus the bitter fraction separates with the methanol/water phase while the non-bitter fraction separates with the hexane. The "hexane layer" is washed with water and evaporated to dryness to yield the non-bitter tasting glucolipid fraction. The "aqueous-methanol layer" is then diluted with water and extracted several more times with hexane; evaporation of the hexane yields the colorless bitter tasting glucolipid fraction.

Compositions of this invention are useful in cosmetic and toiletry formulations for external use, as "low calorie" fat substitutes in food, and as evaporation suppressants, antitranspirants and anti-desiccants. Non-bitter glycolipids are preferred fat substitutes and are also preferred for use in cosmetic applications where taste is of concern.

The 2,3,4-tri-O-acylhexoses of the invention can be synthesized using known chemical methods. Examples of methods suitable for carrying out such syntheses are included below under the heading "Methods for Making 2,3,4-Tri-O-acylhexoses and Mixtures Thereof: Synthesis of 2,3,4-Tri-O-acylhexoses". Although the 2,3,4-tri-O-acylhexoses of the present invention can be synthesized using known chemical methods, some compounds of the present invention, especially 2,3,4-tri-O-acylglucoses and specific mixtures thereof, are preferably obtained by selective organic extraction of the epicuticular exudate from *Lycopersicon pennellii* plant parts, followed by selective purification of components thereof. Methods for extracting the epicuticular exudate from *Lycopersicon pennellii* plant parts, plus methods for purifying the extracted exudate, are included below under the heading "Methods for Making 2,3,4-Tri-O-acylhexoses and Mixtures Thereof: Extraction of 2,3,4-Tri-O-acylhexoses". Methods for separating the purified extracted exudate into the bitter and non-bitter subfractions are included below under the heading "Separation of *Lycopersicon pennellii* Glucolipids into Bitter and Non-bitter Fractions".

The starting materials for the *Lycopersicon pennellii* epicuticular exudate extraction methods are *Lycopersicon pennellii* plants. Such plants are widely available to anyone wishing to use them to make compounds or mixtures of the present invention. For example, seeds of *Lycopersicon pennellii* can be obtained from a variety of public sources. Several such sources are listed below under the heading "Sources of *Lycopersicon pennellii* Plants". Alternatively, *Lycopersicon pennellii* plants and seeds can be obtained from wild populations growing along the western coast of Peru.

*Lycopersicon pennellii* natural plant extract (i.e., the *Lycopersicon pennellii* extraction product mixture recovered following evaporation of the extraction solvent) is a mixture of compounds comprising an alkane fraction and a glucolipid fraction plus minor (less than 1%) amounts of terpenes.

The "alkane fraction" accounts for about <5–10% of the extracted epicuticular exudate mixture. This fraction is actually comprised of many constituent molecules, including iso $C_{27}$, normal $C_{27}$, iso $C_{28}$, anteiso $C_{28}$, normal $C_{28}$, iso $C_{29}$, normal $C_{29}$, iso $C_{30}$, anteiso $C_{30}$, normal $C_{30}$, iso $C_{31}$, normal $C_{31}$, iso $C_{32}$, anteiso $C_{32}$, normal $C_{32}$, iso $C_{33}$, normal $C_{33}$, iso $C_{34}$, anteiso $C_{34}$ and normal $C_{34}$ alkanes. Of the three fractions making up the total extract, the alkane fraction is the least polar.

The "glycolipid fraction" (also referred to herein as the "G" fraction) accounts for about 90–95+% of the total extracted epicuticular exudate mixture. Our analyses (see the heading "Separation of Glycolipid Components") show that the glycolipid (G) fraction is highly polar, and is really composed of a group of molecules that are representative of a new class of compounds. As discussed above, the members of this class are comprised of a hexose (e.g., glucose) molecule O-acylated at the 2,3, and 4 positions with normal-, iso-, and/or anteiso-alkanoic acids containing three to eighteen carbons.

When at least one of the acylating fatty acid groups on the hexose molecule is a normal, iso-, or anteiso-, alkanoic or alkenoic fatty acid having eight or more carbons, the resulting 2,3,4-tri-O-acylhexoses (or mixtures thereof) have a non-bitter taste. On the other hand, when none of the acylating fatty acids have more than 7 carbons, the resulting 2,3,4-tri-O-acylhexoses (and mixtures that contain them) are bitter when tasted.

The extracted *Lycopersicon pennellii* epicuticular exudate can be purified using known methods such as liquid/liquid extraction. An example of such an extraction is illustrated below under the heading "Purification of Components of the Epicuticular Exudate". When we purified the components of the total extract (TE) using the exemplified liquid/liquid extraction procedure, we found that about 88% of the *Lycopersicon pennellii* epicuticular exudate (TE) was comprised of a polar glucolipid extract (G) fraction, and about 12% was comprised of non-polar extract fraction. With other extraction methods (data not shown) we found that the polar glucolipid fraction comprised about 95%+ of the total extract, while non-polar components comprised the remaining ~5%.

As taught herein, the polar *Lycopersicon pennillii* glucolipid fraction can be further separated into two fractions, one of which is bitter, the other of which is not. The preferred method for separating and purifying the fractions is outlined in Table 1, infra. According to the method, *Lycopersicon pennellii* epicuticular exudate is first extracted from *Lycopersicon pennellii* plant parts using a suitable organic solvent such as methylene chloride. The solvent is then removed from the raw exudate by suitable means such as evaporation. The dry, solvent free exudate is then dissolved in a suitable solvent such as methanol. The resulting solution is first cooled to aid in the crystallization of the alkanes present in the raw exudate, and then filtered to separate the solid alkane crystals from the methanol/glucolipid solution. The remaining methanol/glucolipid solution is then decolorized to remove the color (e.g. chlorophyll) from the glucolipid product. (An important constraint on the purification scheme is the order of the alkane removal and decolorization steps. In order for the color to be effectively removed, the alkanes must be removed from the solution first. The preferred method, therefore, has the crystallization and filtration steps before the decolorization step.) Water is added to the filtered, decolorized methanol/glucolipid solution to attain an approximate ratio of 4:1, $MeOH:H_2O$. This aqueous methanol solution is extracted once with hexane. Water is further added to this hexane-washed aqueous MeOH solution to obtain a ratio of approximately 2:1, $MeOH:H_2O$. This diluted solution is then extracted at least twice with hexane to yield a hexane/non-bitter glucolipid phase and a methanol/water/bitter glucolipid phase. The non-bitter phase is washed again with water and then evaporated to dryness to yield colorless, non-bitter glucolipid. The aqueous MeOH washings are combined, and then extracted with hexane. Evaporation of the hexane yields the colorless bitter glucolipid.

In the preferred extraction method of the invention the ratio of mixed $MeOH/H_2O$ is fairly critical. However, neither the contact time, the number of washings, nor the volume of each washing is critical and each may vary.

Many of the acylating alkanoic acids present in the glycolipid fraction are rare and useful. For example, the glycolipid fraction contains 8-methylnonanoic acid which can be used to make synthetic lubricants. The fraction also contains 2-methylpropanoic, 3-methylbutanoic and 2-methylbutanoic acids, all of which have many uses, including flavors and fragrances. Following hydrolysis, these specific fatty acids or any of the constituent acyl groups can be extracted and purified for use as desired.

Compositions of the invention are useful as evaporation suppressants, antitranspirants and antidesiccants. When used in this manner, the glycolipid fraction (G) is preferably not separated from the total *Lycopersicon pennellii* epicuticular extract (TE). Experiments illustrating use of the *Lycopersicon pennellii* epicuticular extract (and its glycolipid fraction) as evaporation suppressants are outlined in Example 1. Such experiments show that both the *Lycopersicon pennellii* glycolipid fraction (G) and the total epicuticular exudate extract (TE) have the ability to inhibit water loss. Thus both can be applied to bodies of water, such as irrigation ponds, municipal water reservoirs, and waste-water treatment ponds to inhibit evaporation. The experiments included in Example 2 illustrate successful use of *Lycopersicon pennellii* natural plant extract as an antitranspirant and antidesiccant.

Compositions of the present invention are also useful as ingredients in cosmetics and toiletries when the compositions are used in combination with at least one suitable standard cosmetic or toiletry ingredient.

For example, new cosmetic and toiletry compositions can be made by combining *Lycopersicon pennellii* natural plant extract, either as TE (or the G, NBG, or BG subfractions thereof,) with suitable standard cosmetic and toiletry ingredients. For purposes of the present invention standard cosmetic and toiletry ingredients that *Lycopersicon pennellii* natural plant extract can be combined with to create new and useful cosmetic and toiletry compositions include, but are not limited to, fragrances, pigments, preservatives, antioxidants, stabilizers, solubilizers, emollients, barrier agents, healing agents, humectants, emulsifiers, and the like, plus compounds on a list of standard cosmetic and toiletry ingredients provided by Fox ("Skin Care: An Overview and Update on the State of the Art and Science", Cosmetic & Toiletries, Volume 99, March, 1984 at pages 46–52). The Fox list is the result of an analysis of approximately 125 leading skin care products; it includes and classifies the standard ingredients as being (a) moisturizers and emollients such as hydrocarbons, polyols, lanolin and its derivatives, silicones, fatty acids, fatty alcohols, esters, triglycerides, amino acids and polypeptides; (b) emulsifying agents such as soaps, esters, fatty alcohols, polymers, sterols, ethers, and surfactants; (c) preservatives; (d) antioxidants; (e) stabilizers; and (f) speciality ingredients such as U.V. absorbers, vitamins and precursors, hormones, plant extracts, nucleic acids, bee jelly, cell extracts, mineral salts, egg powder, flour, etc. The Fox list also includes examples of each standard ingredient category. For instance, Fox lists dimethicone, cyclomethicone, dimethicone copolyol, phenyl dimethicone and steroxy dimethicone as being examples of standard "silicones" found in leading skin care products. For the sake of brevity the numerous and various examples given in the Fox list are not listed herein, but are expressly incorporated herein by reference.

Depending on the particular purpose for which the cosmetic or toiletry composition is being formulated, those skilled in the art, in accordance with common practice, can combine *Lycopersicon pennellii* natural plant extract with these known standard ingredients to produce new creams, lotions, shampoos, soaps, lipsticks, eye creams, milks, rouges, make-ups, foundations, deodorants, antiperspirants, conditioners, hair grooming products, shaving products, sun care products, bath products, and the like. In general, when making these new compositions, both the *Lycopersicon pennellii* natural plant extract and the known standard ingredients should be of a quality or purity (such as U.S.P. or N.F.) suitable for cosmetic use.

Examples of such new *Lycopersicon pennellii* natural plant extract containing cosmetic and toiletry compositions are included below (*See* Examples 4–22) to illustrate the variety of ways the *Lycopersicon pennellii* natural plant extract can be utilized to make new and useful cosmetic and toiletry products. For instance, Example 4 demonstrates the usefulness of *Lycopersicon pennellii* natural plant extract as an ingredient in skin lotions. More specifically, Example 4 shows that *Lycopersicon pennellii* natural plant extract can be combined with mineral oil and a common surfactant to produce a skin lotion that stays completely in emulsion, has a pleasant whitish appearance and a pleasant soft feel. In a similar vein Example 6 illustrates use of *Lycopersicon pennellii* natural plant extract as an ingredient in a skin cream. Again, as in Example 4, *Lycopersicon pennellii* is used in combination with known standard cosmetic and toiletry ingredients to produce a cosmetic product that stays in emulsion, has an attractive color and a pleasant feel.

Example 3 is included to demonstrate that when *Lycopersicon pennellii* natural plant extract is used in cosmetic compositions, the *Lycopersicon pennellii* glycolipid-containing epicuticular extract functions as a moisture barrier. Examples 8 through 22 are included to illustrate the range of cosmetic and toiletry formulations to which *Lycopersicon pennellii* natural plant extract can be added. These same examples also illustrate the range of functions *Lycopersicon pennellii* natural plant extract can serve in such compositions, e.g., as an emollient, a moisture barrier, a thickening agent, a source of color, etc.

Examples of such new *Lycopersicon pennellii* epicuticular exudate bitter and non-bitter fraction containing cosmetic and toiletry compositions are included below (*see* Examples 19–22) to illustrate the variety of ways the *Lycopersicon pennellii* epicuticular exudate bitter and non-bitter fraction can be utilized to make new and useful cosmetic and toiletry products. For instance, Example 19 demonstrates the usefulness of *Lycopersicon pennellii* epicuticular exudate bitter subfraction as an ingredient in baby cream. The bitter taste discourages accidental ingestion of the product. Example 20 illustrates use of the bitter fraction as an ingredient in nail polishes. The bitter taste discourages nail biting. (Solutions of bitter glycolipid can also be painted onto children's thumbs to discourage thumb sucking.)

Examples 21 and 22 are included to illustrate use of *Lycopersicon pennellii* epicuticular exudate non-bitter fraction as an ingredient in cosmetic products where taste is of concern. Example 21 shows use of the non-bitter fraction as an ingredient in lip balms, while Example 22 shows its use in lipsticks.

Many of the formulations included in the examples that follow are modifications of known cosmetic and toiletry compositions. *See* Flick, 1984. Such modifications illustrate the range of usefulness of *Lycopersicon pennellii* natural plant extract as an ingredient in cosmetic and toiletry formulations. Such modifications also illustrate the ease with which those skilled in the art can utilize *Lycopersicon pennellii* natural plant extract for this purpose.

When those skilled in the art make new *Lycopersicon pennellii* natural plant extract containing cosmetic and toiletry products, the *Lycopersicon pennellii* natural plant extract can be combined with the other standard ingredients according to conventional admixing techniques. For example, the components may be added at once or successively to a mixing vessel and admixed using standard stirring or agitation means. Such methods for combining the *Lycopersicon pennellii* natural plant extract with known cosmetic and toiletry ingredients are not critical.

Knowing that *Lycopersicon pennellii* natural plant extract would be included in products used by human beings, its safety for this purpose was checked using standard methods. Based on the results of standard animal toxicity tests, animal and human skin irritation tests, and an animal ocular irritation test, *Lycopersicon pennellii* natural plant extract is believed to be nontoxic and nonirritating and therefore deemed to be safe for human use. The safety tests are included below.

Compositions of the present invention are useful as foods, either by themselves or in combination with suitable standard food ingredients.

As discussed above, the glycolipid (G) fraction of the *Lycopersicon pennellii* natural plant extract is comprised of a mixture of 2,3,4-tri-O-acyglucoses. As also discussed above, at room temperature the G fraction is a colorless, clear, oily liquid. Thus the G fraction has physical properties characteristic of many ordinary triglyceride oils. However, unlike ordinary triglyceride fats or oils that have all three hydroxyl groups of glycerol esterified with fatty acids, the G fraction is made up of 2,3,4-tri-O-acylglucoses each having a free primary hydroxyl.

Pancreatic lipase is an enzyme found in animal systems that hydrolyzes the esters of primary alcohols. When triglyceride fats or oils are exposed to pancreatic lipase, the enzyme catalyzes the hydrolysis of triglycerides to yield free fatty acids and the glycerol backbone. By doing this the enzyme makes the fatty acids available for absorption, which in turn results in the addition of calories from the metabolism of free fatty acids.

Since the primary hydroxyls on the 2,3,4-tri-O-acylglucoses are free, we hypothesized that the pancreatic lipases might not be able to effectively remove the acylating fatty acids from the glucose molecule. When we tested this hypothesis by incubating a sample of *Lycopersicon pennellii* natural plant extract with pancreatic lipase we found that the *Lycopersicon pennellii* 2,3,4-tri-O-acylglucoses were hydrolysed at rates that were far below those of conventional triglyceride oils. (See the section heading entitled "Hydrolysis of G Fraction by Pancreatic Lipase".)

Knowing that the G fraction of *Lycopersicon pennellii* natural plant extract might be used in food products that would be ingested by human beings, its safety for this purpose was first checked by having an independent testing laboratory run an animal toxicity test. The results of these animal tests indicated that the *Lycopersicon pennellii* natural plant extract is non-toxic when ingested by laboratory animals. (Data not shown.)

Knowing that the *Lycopersicon pennellii* natural plant extract was non-toxic when ingested by laboratory animals, and was hydrolyzed by pancreatic lipase at rates far below those of conventional triglyceride oils, animal studies were conducted to determine the degree of "undigestibilty" of *Lycopersicon pennellii* G fraction. For this study a bolus quantity (approximately 2 grams) of radioactively labeled *Lycopersicon pennellii* $^{14}$C-glucolipid was delivered by intubation into the stomachs of laboratory rats. During a 51 hour post-intubation period, the expired $^{14}CO_2$ was collected on an hourly basis. At the end of 51 hours the animals were sacrificed and the distribution of $^{14}$C-glucolipid in various body compartments (feces, carcass, urine, $^{14}CO_2$ and gastrointestinal contents). Three separate studies were conducted using two separate samples of $^{14}$C glucolipid. Combined results from the three studies showed that about 49% (range 43%–59%) of the glucolipid was not absorbed, while approximately 43.6% (range 33%–51%) was digested, absorbed and metabolized after 51 hours. This compares to about 93% absorption and metabolism of a corn oil control during the same 51 hour time period. The majority of nonabsorbed glucolipid was found in the feces (36.3±5.3% remaining in the gastrointestinal tract contents. (Test procedures and results are detailed below under the heading "Glucolipid Animal Feeding Trial".)

Since the fatty acids on the 2,3,4-tri-O-acylglucoses are not effectively hydrolyzed by the action of the pancreatic lipase, the *Lycopersicon pennellii* G fraction does not make available to the body as many free fatty acids as do conventional fats and oils. Unfortunately, since the *Lycopersicon pennellii* G fraction contains both the bitter and non-bitter subfractions, the G fraction has a bitter taste. For that reason the non-bitter subfraction (referred to herein as the NBG fraction) is preferred for use as a partial or total replacement for ordinary triglyceride fat in any fat containing food composition to provide low calorie benefits. (The 2,3,4-tri-O-acylhexoses, the NBG fraction and food compositions containing them, which are low in available calories, are conveniently referred to herein simply as "low calorie".) The low calorie NBG fraction can also be used as a partial or complete replacement for ordinary triglyceride fat in fat containing food products such as mayonnaise, margarine and dairy products. Depending on the particular purpose for which the food composition is being formulated, those skilled in the art, in accordance with common practice, can combine *Lycopersicon pennellii* NBG fraction with known standard and suitable food ingredients to produce new low calorie breads, cakes, candies, cookies, frostings, gravies, ice creams, margarines, mayonnaises, meat fillings, pates, pie crusts, pie fillings, puddings, sauces, soups, spreads, vegetable fillings and the like. Known standard and suitable food ingredients which *Lycopersicon pennellii* NBG fraction can be combined with, to produce new low calorie food formulations, include but are not limited to baking powders and sodas, bouillons, breads, cheeses, chocolates, coconuts, colorings, creams, eggs, fats, flours, flavorings, fruits, gelatins, herbs, lards, meats, milks, nuts, oils, preservatives, proteins, spices, stabilizer, stocks, sugars, vegetables, vinegars, vitamins, and the like.

As Examples 24 and 25 illustrate, the low calorie *Lycopersicon pennellii* NBG fraction can be used as partial or complete replacement for ordinary triglyceride oil in a salad or cooking oil, or it can be used in frying, baking or the like. In addition, as stated above, the NBG fraction can be used as a substitute for almost any oil or fat in almost any food. To obtain a significant low calories effect, it is preferred that at least about 5% of the fat or oil in the food composition comprises the low calorie *Lycopersicon pennellii* NBG fraction. On the other hand, very low calorie and thus highly desirable food compositions of the invention are obtained when the NBG fraction is used in amounts up to about 99.9%. Low calorie results can also be achieved when *Lycopersicon pennellii* NBG fraction is used as a 100% substitute for conventional cooking oils that are routinely used for frying.

When substantial amounts of the NBG fraction are used in food compositions it may be necessary, if such foods are likely to be consumed in substantial amounts, to fortify the low calorie foods with sufficient fat soluble vitamins (such as vitamin A, vitamin D, vitamin E and vitamin K, or mixtures thereof).

As stated above, examples illustrating use of *Lycopersicon pennellii* NBG fraction as a low calorie food ingredient are included below (*see* Examples 23-25). For instance, Example 23 demonstrates the usefulness of *Lycopersicon pennellii* NBG fraction as an ingredient in a margarine-like food spread. Example 24 illustrates use of *Lycopersicon pennellii* NBG fraction as an ingredient in pancakes and Example 25 shows use of the NBG fraction in making a salad dressing.

The food formulations included in the examples that follow are modifications of known recipes. Such modifications illustrate the range of usefulness of *Lycopersicon pennellii* NBG fraction as a low calorie ingredient in foods. Such modifications also illustrate the ease with which those skilled in the art can utilize *Lycopersicon pennellii* NBG fraction as a low calorie fat substitute in foods.

Without further elaboration, it is believed that one of ordinary skill in the art can use the preceding description to make the novel 2,3,4-tri-O-acylhexoses of the present invention and to utilize them in a variety of ways. As stated above, the examples that follow are included for illustrative purposes only and therefore should not be construed as being limitative in any way of the appended claims.

Sources of *Lycopersicon pennellii* Plants

Seeds of *Lycopersicon pennellii* can be obtained from a variety of public sources. Such sources include the United States Department of Agriculture National Seed Storage Laboratory at Fort Collins, Colo.; the Tomato Genetics Stock Center, the University of California, at Davis, Calif.; the Universidad Nacional Agraria, La Molina, Lima, Peru, as well as wild populations found along the coast of Peru. As a seed source we suggest the Tomato Genetics Stock Center at the University of California. Anyone wishing *Lycopersicon pennellii* seeds from the U.C. Stock Center can obtain them by requesting samples of LA 716, LA 750, LA 751, LA's 1272-1273, LA 1275, LA 1277, LA 1282, LA 1297, LA 1299, LA's 1302-03, LA 1340, LA 1356, LA 1367, LA 1376, LA 1515, LA 1522, LA 1649, LA's 1656-57, LA 1674, LA 1693, LA 1724, LA's 1732-35, LA 1809, LA's 1911-12, LA 1920, LA's 1940-43, or LA 1946.

Botanical Description of *Lycopersicon pennellii*

*Lycopersicon pennellii* (Corr.) D'Arcy was previously known as *Solanum pennellii* Corr. The name change occurred in 1982. A complete botanical description of the species is found in: D'Arcy, W. G., 1982, Combinations in Lycoperiscon (Solanaceae), Phytologia 51:240. That description of the species is expressly incorporated by reference herein.

Methods for Making 2,3,4=Tri-O-acylhexoses, and Mixtures thereof

Sythesis of 2,3,4-tri-O-acylhexoses

The 2,3,4-tri-O-acylhexoses of the present invention can be synthesized chemically by known methods. For example, to incorporate three identical acyl groups at the 2, 3 and 4 positions on the hexose moiety, the following method can be used. One molar equivalent of hexose is mixed with two molar equivalents of trityl chloride in dry pyridine. The resulting mixture is shaken vigorously, then stirred for several days. A suspension of this mixture is mixed with three molar equivalents of acyl chloride in chloroform. After standing overnight, the mixture is diluted with cold, 2% aqueous bicarbonate, extracted with chloroform, dried over anhydrous sodium sulfate and purified by preparative thin layer chromatography in acetone/hexane (1:5) to yield 1,6-di-O-trityl-2,3,4-tri-O-acylhexose. The blocking group is removed, e.g. by stirring overnight with PtO$_2$ in an atmosphere of hydrogen, filtration, partial removal of the solvent in vacuo, and partitioning between hexane and MeOH/H$_2$O (75:25). When necessary the product can be further purified by reverse phase preparative TLC in MeOH/H$_2$O (70:30).

Hexoses containing mixed acyl substituents can also be synthesized easily using known chemical methods. Thus, for example, readily available 4,6-benzylidene-alpha-1-0-methyl-hexose can be acylated with one equivalent of acyl chloride (R$^1$Cl) in dry chloroform and pyridine, followed by the addition of a second equivalent of acyl chloride (R$^2$Cl) to give 2,3-di-O-acyl-4,6-benzylidene-alpha-methyl-hexose. After removal of the benzylidene moiety with hydrogen over platinum, the 6-hydroxyl can be reprotected with a slight molar excess of trityl chloride in pyridine. This product can be acylated with one equivalent of a third acyl chloride and deprotected, e.g. by hydrogenation over platinum to give 2,3,4-tri-O-acyl-alpha-methylhexose, where the acyl groups have been specifically selected. The methyl group can be removed by mild acid hydrolysis.

Detailed methods for synthesizing the 2,3,4-tri-O-acylhexoses of the present invention are outlined in the following examples. As stated above, such examples are for illustrative purposes only and are not intended to limit in any way the scope of the claims.

In general, reaction temperature is not critical in these synthetic methods so the reactions are usually carried out under cooling or at ambient temperature. In addition, chemists skilled in the art will recognize that a variety of solvents other than those listed will be useful in preparing these and similar derivatives.

(a) To illustrate synthesis of a 2,3,4-tri-O-acylhexose wherein the acylating groups are identical, the synthesis of 2,3,4-tri-O-isobutanoyl-D-glucopyranose (see FIG. 1) is described:

Anhydrous glucose (1 molar equivalent), trityl chloride (2 molar equivalents) and dried pyridine, as solvent, were shaken vigorously and set aside with magnetic stirring for several days. This provided a stock solution of 1,6-ditrityl glucose, referred to herein and in FIG. 1 as compound I, in pyridine. (Other 1,6-ditrityl hexoses could be prepared in the same manner by using hexoses other than glucose.)

An aliquot of stock solution, I, was removed and a 3-fold molar amount of a solution of isobutyroyl chloride in chloroform was added; then the resulting mixture set aside overnight. The next day the mixture was diluted with cold 2% aqueous bicarbonate and extracted with chloroform, dried over anhydrous sodium sulfate and subjected to preparative TLC on silica gel plates with acetone/hexane (1:5). The 1,6-ditrityl glucose, I, so treated yielded 1,6-di-O-trityl-2,3,4-triisobutanoyl-D-glucopyranoside, referred to herein and in FIG. 1 as compound II.

Compound II in dioxan (1 ml) was stirred overnight in a 10 ml flask with PtO$_2$ in an atmosphere of hydrogen. The resulting mixture was filtered through Celite and after removal of the solvent in vacuo the product was partitioned between hexane and MeOH/H$_2$O (75:25). The product of the polar layer gave essentially two bands by reversed phase preparative TLC in MeOH/H$_2$O (70:30). The major higher R$_f$ band was identical to the natural 2,3,4-tri-O-acylglucose, referred to herein and in FIG. 1 as compound III, extracted from *Lycopersicon pennellii* plant parts. Hexose sugars other than glucose, for example galactose and mannose, can be acylated by the same procedure to give corresponding 2,3,4-tri-O-acylhexoses.

(b) To illustratrate synthesis of a "mixed" 2,3,4-tri-O-acylhexose, synthesis of mixed 2,3,4-tri-O-acyl-methyl-D-glucoside (see FIG. 2) is described.

4,6-Benzylidene-alpha-methyl-D-glucoside was singly acylated using one equivalent of R$^1$-acyl chloride in dry chloroform and pyridine. A second acylation with an additional equivalent of R$^2$-acyl chloride gave 2,3-diacyl-4,6-benzylidene-alpha-methyl-D-glucoside. The benzylidene moiety was then removed (H$_2$/PtO$_2$) and the 6 hydroxyl was reprotected (trityl chloride in pyridine). This product was acylated with one equivalent of a third acyl chloride, and deprotected (H$_2$/PtO$_2$) to give 2,3,4-tri-O-acyl-alpha-methyl-D-glucoside. The 2,3,4-tri-O-acylglucose is made by mild acid cleavage of the glucoside. Hexose sugars other than glucose, such as galactose and mannose, can be acylated by the same procedure to give corresponding mixed 2,3,4-tri-O-acylhexoses.

In both syntheses just described, all intermediates and products were satisfactorily identified using NMR, TLC, HPLC and MS when necessary and appropriate.

Methods for Making 2,3.4-Tri-O-acylhexoses, and Mixture thereof

Extraction of 2,3,4-tri-O-acylhexoses

The 2,3,4-tri-O-acylhexoses of the present invention (and mixtures thereof) are preferably obtained by selective extraction and purification of the epicuticular exudate from *Lycopersicon pennellii* plant parts, followed by selective purification of components thereof.

The 2,3,4-tri-O-acylhexoses of the present invention make up the bulk of the *Lycopersicon pennellii* epicuticular exudate. Since the 2,3,4-tri-O-acylhexoses are glycolipids, the 2,3,4-tri-O-acylhexoses can be extracted from the *Lycopersicon pennellii* plant parts using lipid extraction methods.

General methods for extracting lipids and lipid-like compounds from plants are well known and well described in the scientific literature. Any of these known methods can be used to extract the *Lycopersicon pennellii* epicuticular glycolipids as long as such methods allow the epicuticular glycolipids to be obtained in: (a) good yield, and (b) without being contaminated by lipids (e.g., the chlorophylls) normally found deeper within the plant. These objectives can easily be achieved by those skilled in the art, using standard techniques, by choosing a suitable solvent and by limiting the time of exposure of the plant parts to the solvent.

On a commercial scale, harvesting and processing equipment are readily available that can handle the *Lycopersicon pennellii* plant material, lipid extraction, solvent evaporation, and purification of the extracted fractions. On a laboratory scale, the whole *Lycopersicon pennellii* plant, or various parts thereof, can either be dipped into or contacted by any one of a number of solvents, including chloroform, hexane, or methylene chloride. Suitable extraction times will vary according to the solvent being used, but will often range from about ten seconds to about ten minutes. An extraction time of about one minute is typical for chloroform. The extracted epicuticular lipids can then be recovered by evaporating the solvent.

Separation of *Lycopersicon pennellii* Glucolipid into Bitter and Non-Bitter Fractions A preferred method for purifying and separating the non-bitter and bitter glucolipids contained within the *Lycopersicon pennellii* epicuticular exudate extract is discussed above under the heading "Detailed Description of the Invention". This preferred method is also outlined in Table I, below.

As stated above, on a commercial scale, harvesting and processing equipment are available that can handle the *Lycopersicon pennellii* plant material, glycolipid extractions, filtrations, solvent evaporations and purifications of the extracted fractions. To illustrate such commercial production we used a 300 gallon reactor to extract *Lycopersicon pennellii* glycolipid and then separate it into bitter and non-bitter fractions as follows:

The raw exudate/methylene chloride mixture was first charged into the reactor; dirt and other debris were then filtered from it. The methylene chloride was stripped from the exudate, then methanol was added to redissolve the glucolipids. The solution was then chilled to promote crystallization of the alkanes. As the reactor contents are drained, the crystals were filtered and the solution treated with activated charcoal to remove color. A portion of this solution was diluted with water and then washed three times with hexane. Then, the hexane/non-bitter layer was washed with methanol/water and then water before the hexane was stripped to yield the non-bitter glucolipid product. The three methanol/water layers were further diluted with water and then extracted with hexane to yield the bitter glucolipid product.

Analysis of Extracted Epicuticular Exudate with Thin Layer Chromatography

The extracted epicuticular exudate can be analyzed by known methods, including thin layer chromatography (TLC). In analyzing the extracted epicuticular exudate with TLC, the unfractionated sample is applied to the start line of a thin layer plate. The plate is then developed using a suitable solvent system. After the chromatogram is developed and solvents are evaporated off, the resolved compounds are detected by: (a) exposure to iodine vapors to detect all components on the plate, (b) spraying with orcinol spray (0.55% orcinol, 0.9% ferrichloride, 5% sulfuric acid in ethanol) to detect sugars, and (c) spraying with ferric chloride spray (0.05% $FeCl_3.6H_2O$ in water/sulfuric acid/acetic acid, 90/0.5/5), to detect sterols (red color on heating the plate).

When we examined the composition of the extracted epicuticular exudate mixture by TLC on silica gel G (Whatman) using a solvent mixture of hexane:diethyl ether:glacial acetic acid in the proportions 60:40:2, the hydrocarbon fraction had an $R_f$ of 0.9; the terpenoids an $R_f$ of 0.5, the flavonoids an $R_f$ of 0.3; and the glycolipids an $R_f$ of 0.15.

By way of example, in analyzing the extracted epicuticular exudate with TLC, the unfractionated sample is applied to the start line of a thin layer plate of silica gel. The plate is then developed using a suitable solvent system. After the chromatogram is developed and solvents are evaporated off, the resolved compounds are detected by: (a) exposure to iodine vapors to detect all components on the plate, (b) spraying with orcinol spray (0.55% orcinol, 0.9% ferrichloride, 5% sulfuric acid in ethanol) to detect sugars, and (c) spraying with ferric chloride spray (0.05% $FeCl_3.6H_2O$ in water/sulfuric acid/acetic acid, 90/0.5/5), to detect sterols (red color on heating the plate).

When we examined the composition of the extracted epicuticular exudate mixture by TLC on silica gel G (Whatman) using a solvent mixture of hexane:diethyl ether:glacial acetic acid in the proportions 60:40:2, the hydrocarbon fraction had an $R_f$ of 0.9; the terpenoids an $R_f$ of 0.5, and the glycolipids an $R_f$ of 0.15.

Purification of Components of the Epicuticular Exudate

The extracted *Lycopersicon pennellii* epicuticular exudate can be purified by known methods, including liquid/liquid extraction. By way of example, in purifying the total extract (TE) by liquid/liquid extraction, a sample of the total crude extracted epicuticular lipid mixture is dissolved in hexane and the solution clarified by refluxing for fifteen minutes with activated charcoal.

After cooling and removal of the charcoal by filtration the hexane solution is partitioned sequentially with methanol:water (80:20) (1x), then methanol:water (75:25) (3x). At each stage, after thoroughly shaking, the layers are separated and the aqueous methanol layers combined. The methanol:water combined extracts are washed once with hexane and the latter combined with the other hexane layer.

When we purified the components of the total extract (TE) using this exemplified liquid/liquid extraction procedure we found that removal of the solvent from the methanol-water combined layer gave a polar glycolipid extract fraction (G) that comprised from about 88% to about 95% of the *Lycopersicon pennellii* epicuticular exudate (TE). In this example, removal of hexane from combined hexane extracts gave non-polar extracts that together comprised from about 5% to about 12% of the *Lycopersicon pennellii* epicuticular exudate.

Separation of Glucolipid Components

Separation of the polar glucolipid extract fraction (G) into individual components can be achieved by High Performance (Pressure) Liquid Chromatography (HPLC), using C-18 reverse-phase column, either on analytical or preparative scale. It may also be achieved under isocratic or gradient conditions.

Example of isocratic conditions

The polar glucolipid extract (G) freed from non-polar components (see heading "Purification of Components of the Epicuticular Exudate", above) was dissolved in HPLC grade acetonitrile and filtered through a Millex-SR 0.5 micron filter unit. A portion of the resulting solution was injected onto a micro-Bondapak TM-C-18 column (30 cm×7.8 mm). The eluting solvent system was acetonitrile:water (75:25) at a flow rate of 1.5 ml/min, with UV-detection at 210 nm. The appropriate fractions were collected and kept on ice throughout the purification. If left overnight, solutions were stored at $-18°$ C. Fractions were evaporated using a rotary evaporator with a bath temperature not exceeding 42° C. The residues were stored in a desiccator. In this manner, several glucolipids were isolated, each in its separate anomeric state, alpha and beta. These glucolipids are shown by the following formulas.

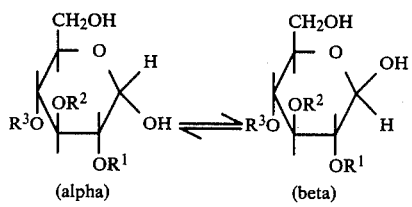

1. $R^1,R^2,R^3 = 3(CH_3)_2CHC=O$
2. $R^1,R^2,R^3 = 2\times(CH_3)_2CHC=O; CH_3CH_2(CH_3)CHC=O$
3. $R^1,R^2,R^3 = 2\times(CH_3)_2CHC=O; (CH_3)_2CHCH_2C=O$
4. $R^1,R^2,R^3 = 2\times(CH_3)_2CHC=O; (CH_3)_2CH(CH_2)_6C=O$
5. $R^1,R^2,R^3 = 2\times(CH_3)_2CHC=O; CH_3(CH_2)_8C=O$
6. $R^1,R^2,R^3 = (CH_3)_2CHC=O; CH_3CH_2(CH_3)CHC=O, (CH_3)_2CH(CH_2)_6C=O$
7. $R^1,R^2,R^3 = (CH_3)_2CHC=O; (CH_3)_2CHCH_2C=O, (CH_3)_2CH(CH_2)_6C=O$
8. $R^1,R^2,R^3 = (CH_3)_2CHC=O; CH_3CH_2(CH_3)CHC=O, CH_3(CH_2)_8C=O$
9. $R^1,R^2,R^3 = (CH_3)_2CHC=O; (CH_3)_2CHCH_2C=O, CH_3(CH_2)_8C=O$ Gradient conditions The polar glycolipid extract (G) was separated in a similar fashion on HPLC using a gradient profile as follows:

| Time | Solvent |
|---|---|
| 0–6 min | acetonitrile:water (50:50) |
| 6–8 min | gradual change to acetonitrile:water (80:20) |
| 8–16 min | acetonitrile:water (80:20) |
| 16–18 | change to acetonitrile 100% |
| 18–30 min | acetonitrile 100% |
| 30–new injection | re-equilibration with acetonitrile:water (50:50) |

The profile and order of elution of glycolipid components were similar under isocratic and gradient conditions. The isocratic condition was simpler and more practical, especially for the preparative separation.

The fatty acid composition of the unfractionated glucolipid fraction (G) as determined by a variety of tests (data now shown), is typically about 41% 2-methylpropanoic acid (iso $C_4$), about 4% 3-methylbutanoic acid (iso $C_5$), about 4.5% 2-methylbutanoic acid (anteiso $C_5$), about 31.5% 8-methylnonanoic acid (iso $C_{10}$), about 10.5% decanoic acid (n $C_{10}$) with trace amounts of methyl decanoic acid, n-undecanoic acid and n-dodecanoic.

The fatty acid substituents are often found to follow certain patterns; thus the acid composition is approximately:

1. $3\times$ iso $C_4$
2. $2\times$ iso $C_4$, anteiso $C_5$
3. $2\times$ iso $C_4$, iso $C_5$
4. $2\times$ iso $C_4$, iso $C_{10}$
5. $2\times$ iso $C_4$, n$C_{10}$
6. iso $C_4$, anteiso $C_5$, iso $C_{10}$
7. iso $C_4$, iso $C_5$, iso $C_{10}$
8. iso $C_4$, anteiso $C_5$, n $C_{10}$
9. iso $C_4$, iso $C_5$, n $C_{10}$ Safety Tests To test Whether *Lycopersicon pennellii* plant extract is safe for use in compounds to be ingested by or used externally on humans, an independent testing laboratory tested the safety of the total extract (TE) by subjecting it to the following tests. (Data is not included for a standard animal toxicity test that showed the *Lycopersicon pennellii* natural plant extract is non-toxic to laboratory rats.) (When discussing the animal tests the neat liquid is at times referred to as "the test article".)

Animal Skin Irritation Tests

To test whether *Lycopersicon pennellii* plant extract (TE) is a primary irritant to rabbit skin, six (6) New Zealand white rabbits, weighing approximately 2 kilograms and being about 3 months of age, were subjected to the test article in the following manner. Using a slight modification of the technique described in Draize, 1975(a), hair on the back of each test animal was clipped. Within the clipped area two (2) test sites were chosen, one on each side of the vertebral column for each animal. Each test site was 2.5 centimeters square.

The test site on the left side of the animal remained intact; the test site on the right was further prepared by abrading the skin with a sterile 22 gauge hypodermic needle. The abrasions were longitudinal epidermal incisions, sufficiently deep to penetrate the stratum corneum, but not so deep as to destroy the integrity of the derma, i.e., to cause bleeding.

A single application of one half (0.5) of a milliliter neat of the test article was made to each test site. The test article was then covered with a 2.5 cm² surgical gauze pad, which was held in place with adhesive tape.

After both test sites were treated, the entire trunk of each animal was encased in an impermeable occlusive wrapping fixed in place with adhesive tape. This aided in maintaining the test article and patches in position and prevented the evaporation of possible volatile components of the test article.

The wrapping and test article were removed 24 hours following application. Remaining test article was gently wiped from the skin, and each test site was individually examined and scored at 24 and 72 hours for erythema and edema using the Draize skin scoring scale. See Draize, 1975(a).

A Draize score of 5.0 or more indicates a primary dermal irritant. Since the primary irritation index for the test article was 3.38, it was concluded the *Lycopersicon pennellii* total plant extract (TE) is not a primary dermal irritant to rabbits under conditions of this test.

Animal Ocular Irritation Tests

To test whether *Lycopersicon pennellii* plant extract (10% (w/v) TE in corn oil) is an ocular irritant in rabbits, six (6) New Zealand white rabbits, weighing approximately 2 kilograms and being about 3 months of age, were exposed to the test article in the following manner.

Using a slight modification of the techniques described by Draize, 1975(b), the toxicity of *Lycopersicon pennellii* plant extract to ocular mucosa was determined by examining the cornea, iris, and the bulbar and palpebral conjunctivae for the presence of injuries following exposure of the rabbits eyes to the test article. Following such examination numerical scores were assigned to the test animals according to a Draize scale. See Draize, 1975(b). In this system of Draize scoring, the injuries to the cornea and iris account for approximately 80% of the score; according to the scoring procedure these structures are purposely weighted because of their vital role in vision.

Immediately prior to the start of the test, the test animals were placed in wooden restrainers. A dose of one-tenth (0.1) of a milliliter neat of the test article was placed in one eye of each test animal by gently pulling the lower lid away from the eyeball to form a cup into which the test article was dropped. The eyelids were gently held together for 1 second. The contralateral eye, remaining untreated, served as a control. If any of the test article remained in the eye at 24 hours, the eye was washed out with lukewarm water after the 24 hour reading.

Observations of ocular irritation were recorded 24, 48 and 72 hours following installation of the test article. (According to the test procedure, if an animal exhibits any irritation within the first 72 hours, additional readings are made at 4 and 7 days after application.)

An animal was considered as exhibiting a positive reaction if the test article produced any of the following: ulceration of the cornea other than a fine stippling, opacity of the cornea other than a slight dulling of the normal luster, inflammation of the iris other than a slight deepening of the folds or slight circumcorneal injection of the blood vessels, obvious conjunctival swelling with partial eversion of the lids or a diffuse crimson-red with individual vessels not discernible.

If two (2) or more animals exhibited a positive reaction, the test article was considered an ocular irritant (unless the test was repeated with another six (6) animals without positive reactions.)

According to the Draize scale used in this procedure a score of 0.0-0.5 leads to a rating of "non-irritating". Since the test article showed Draize scores of 0.3 at 24 hours, and 0.0 at 48 and 72 hours, it was concluded that *Lycopersicon pennellii* total plant extract (TE) is not an ocular irritant to rabbits under conditions of this test.

Human Skin Irritation Tests

To determine, by epidermal contact, the primary or cumulative irritation and/or sensitization potential of *Lycopersicon pennellii* natural plant extract to humans, a panel comprised of fifty-two adult subjects (forty-four females and eight males), ranging in age from 20-74 years, were subject to the test article as follows. Approximately 0.15 milliliters of the test material, 10% *Lycopersicon pennellii* natural plant extract in corn oil, was applied to a precut 1"×1" Webril pad. This was secured to the treatment site, located on the upper back between the scapulae, with one strip of Dermicel tape to form a semi-occlusive patch.

This procedure was followed three times per week: Monday, Wednesday, and Friday, for a total of ten applications. The treatment site was marked to ensure the continuity of patch application. The participants were instructed to remove this patch after twenty-four hours. The evaluation of the site was made just prior to re-application. Rest periods consisted of twenty-four hours following the Tuesday and Thursday removal, and forty-eight hours following the Saturday removal.

At the conclusion of a fourteen day rest period following the tenth application, a challenge patch was applied to the original site and to a virgin site. Each site was evaluated at twenty-four and forty-eight hours after application. The volar forearm served as the virgin test site.

Fifty-one subjects completed the repeated insult patch test. The remaining subject dropped out for personal reasons unrelated to the use of the test material.

The test sites were rated from 0 (no visible reaction) to 4+ (a reaction showing erythema and edema with vesiculation and ulceration).

The scores for the participants of this test were zero, indicating that none of the participants showed any visible reaction, at any time, to the test compound. Thus it was concluded that under the condition of this test procedure, *Lycopersicon pennellii* natural plant extract does not indicate a potential for dermal irritation or sensitization in humans.

Hydrolysis of G Fraction by Pancreatic Lipase

Pancreatic lipase is an enzyme found in animals and humans that catalyzes the hydrolysis of triglycerides to yield free fatty acids and the glycerol backbone. By doing so, this enzyme makes the fatty acids available for absorption, and consequently, addition of calories from the metabolism of free fatty acids. Pancreatic lipase can catalyze the hydrolysis of esters of primary alcohols. As can be seen from the structure of *Lycopersicon pennellii* 2,3,4-tri-O-acylglucoses, the primary hydroxyls are free. Therefore the glucolipid (or G fraction) should not be hydrolyzed by pancreatic lipase.

To prove such a hypothesis, glucolipid was incubated with porcine pancreatic lipase. The assay of lipase activity was done using commercially available pancreatic lipase. The lipid sample was suspended in 8 ml of 10% gum arabic and 0.1 ml of a 20% sodium taurocholate solution, water was then added to make the volume 9 ml. For the enzymic reaction 1.0 ml of the lipid emulsion was mixed with 1.0 ml of 0.2 M Tris-HCl buffer, pH 7.8, 3.0 ml of 1.5% NaCl, and this mixture was placed in the titration apparatus (Radiometer pH stat). The reaction was started by the addition of enzyme. The reaction mixture was automatically titrated with 3.2 mM NaOH to maintain the pH of 7.8 and the volume of NaOH required was recorded. The system was calibrated by using different concentrations of olive oil to establish the dependence of rate on substrate concentration. The G fraction was tested in this system and was found to be hydrolyzed by the lipase at rates less than 5% of the rates for corresponding amounts of olive oil. These results, and an oral toxicity test which showed *Lycopersicon pennellii* natural plant extract was nontoxic to laboratory animals, (data not shown), suggested that an animal feeding trial could be attempted.

Glucolipid Animal Feeding Trial

To determine the degree of digestion and absorption *Lycopersicon pennellii* glucolipid in laboratory animals, the following feeding trials were run by an independent testing laboratory. A bolus quantity (approx. 2 g.) of radioactively labeled $^{14}C$-glucolipid was delivered to laboratory rats by intubation into the stomach of the animals. Intubation was followed by a 51 hour incubation period during which time expired $^{14}CO_2$ was collected hourly. At the end of 51 hours animals were sacrificed and the distribution of $^{14}C$-glucolipid in the various body compartments (feces, carcass, urine, $CO_2$, and gastrointestinal tract) was determined.

Three separate feeding trials were run using two separate *Lycopersicon pennellii* $^{14}C$-glucolipid samples. The results of the three trials are summarized below:

| Study | Feces | Carcass[a] | Urine | $^{14}CO_2$ | G.I. | Total Recovery |
|---|---|---|---|---|---|---|
| I | 40.8 | 27.2 | 14.9 | 14.0 | 5.6 | 97.4 |
| II | 35.5 | 10.9 | 8.2 | 14.0 | 23.4 | 92.0 |
| III | 32.6 | 11.0 | 9.5 | 26.1 | 10.3 | 89.6 |
|  | 36.3 ($\pm 2.4$)[b] | 14.7 ($\pm 3.7$) | 10.9 ($\pm 2.0$) | 18.0 ($\pm 4.0$) | 13.1 ($\pm 5.3$) | 93.0 ($\pm 2.3$) |

[a] Study I and II carcass = carcass + pelt
[b] Mean ± SEM

Based on the three separate studies the results indicate that about 49% (range 43%–59%) of the glucolipid was not absorbed, while approximately 43.6% (range 33%–51%) was digested, absorbed and metabolized after 51 hours. This compares to about 93% absorption and metabolism of a corn oil control during the same 51 hour time period. The results also indicate that the majority of nonabsorbed glucolipid was found in the feces (36.2±2.4%) with about 13.1±5.3% remaining in the gastrointestinal tract contents.

EXAMPLES

Example 1

This example illustrates the effectiveness of *Lycopersicon pennellii* epicuticular exudate extract, (TE) and its glycolipid fraction (G), as evaporation suppressants.

To test the effect of *Lycopersicon pennellii* total epicuticular exudate extract (TE) and the glycolipid fraction thereof (G) as evaporation suppressants, experiments were performed to test the ability of *Lycopersicon pennellii* (TE) and glycolipid (G) to suppress the evaporation of water. Treatments were applied to atmometers. (Atmometers are instruments standardly used for measurement of evaporation. We used atmometers with ~101 $cm^2$ of surface area; they were provided to us by the Land, Air and Water Resources (LAWR) Department, University of California, Davis, Calif.)

The atmometers were calibrated by allowing them to lose water for 83 minutes, with no treatment applied. The amount of $H_2O$ lost during that period was measured. Treatments were then applied and $H_2O$ loss measured for a like 83 minutes.

Total extract (TE) and glycolipid (G) were dissolved in chloroform. Because the chloroform solvent might have some possible effect on evaporation, a chloroform control was included in the treatments. The following treatments were applied:

1. No treatment
2. Chloroform dip
3. 22.9 mg/$cm^2$ TE dip
4. 0.81 mg/$cm^2$ TE dip
5. 0.081 mg/$cm^2$ TE dip
6. 0.81 mg/$cm^2$ G dip
7. 0.081 mg/$cm^2$ G dip Treatments were replicated and randomized. An analysis of variance was performed on the data; means, standard deviations, and significance are reported in Table 1.

TABLE 1

|  | Treatment | $H_2O$ Lost (% of Control) |
|---|---|---|
| 1. | None | 100.5 ± 0.72 |
| 2. | Chloroform only | 102.7 ± 0.053 |
| 3. | 22.9 mg/$cm^2$ (TE) | 0* |
| 4. | 0.81 mg/$cm^2$ (TE) | 32.8 ± 20.1* |
| 5. | 0.081 mg/$cm^2$ (TE) | 95.8 ± 4.08 |
| 6. | 0.81 mg/$cm^2$ (G) | 50.1 ± 19.1* |
| 7. | 0.081 mg/$cm^2$ (G) | 97.8 ± 3.92 |

*Significantly different from control $^{NB}$ Treatments 4 and 6 are not statistically different, indicating that the activity of TE can be attributed to G.

The results prove that both total extract (TE) and glycolipid fraction (G) are effective evaporation suppressants.

Example 2

This example illustrates the effectiveness of *Lycopersicon pennellii* natural plant extract as an antitranspirant/antidesiccant. To test *Lycopersicon pennellii* natural plant extract as an antitranspirant/antidesiccant the following experiment was run:

1. On day 1 nine flats were seeded (50 seeds/flat) and maintained in a greenhouse. These plants were seeded into "standard" freshly prepared soil mix.
2. One month later the following treatments were applied to the plants:
   a. Control, not sprayed.
   b. Control, sprayed through atomizer with 250 mls. of a solution of 70% acetone:30% water.
   c. Sprayed through atomizer with 250 mls. of a solution of 70% acetone:30% water, into which 250 mg. of *Lycopersicon pennellii* natural plant extract had been dissolved.

Three flats were used for each treatment. The 250 mls. for treatments (b) and (c) were applied evenly over all three flats.
3. As stated above, treatments were applied one month after the flats were seeded. After the application of treatments, flats were placed in a randomized block design, in the greenhouse. They were not watered afterwards. Harvests were made one week after application of the treatment to the plants. At the time of harvest, plants given treatments (a) and (b) were severely wilted.

| 4. Treatment | H$_2$O Loss/ Flat (g) | Fresh Wt. of Plants (g) | Dry Wt. of Plants (g) |
|---|---|---|---|
| (a) | 2552 ± 40 | 134.6 ± 7.4 | 41.7 ± 0.5 |
| (b) | 2536 ± 27 | 124.5 ± 1.4 | 41.5 ± 1.7 |
| (c) | 2453 ± 45** | 153.3 ± 15.1** | 42.2 ± 1.1 |

There was significantly less water loss from the *Lycopersicon pennellii* natural plant extract-treated 'VF36' plants. It is interesting to note that there was no difference in dry weight between the treatments. The results show that *Lycopersicon pennellii* natural plant extract is effective in inhibiting desiccation/transpiration.

Example 3

This example illustrates the effectiveness of *Lycopersicon pennellii* natural plant extract as a moisture barrier in cosmetic and toiletry compositions.

To test the effectiveness of *Lycopersicon pennellii* natural plant extract as a moisture barrier, when the extract is used in combination with other standard cosmetic ingredients, formulations containing *Lycopersicon pennellii* natural plant extract were monitored using standard atmometers. (See Example 1). The formulations tested in this manner include "Lotion I", "Skin Cream I" and "Skin Cream II" as disclosed in Examples 4, 6 and 7 respectively.

The atmometer experiment was performed as follows: the individual atmometers were calibrated by allowing them to lose water for 90 minutes, with no treatment applied. The amount of H$_2$O lost during that period was measured. This measurement was used as a control measurement of atmometer evaporation.

The lotion and skin cream treatments were then applied to atmometers by dipping them into 100 g of solutions of Lotion I, Skin Cream I and Skin Cream II. Each treatment was performed on three replicate atmometers. Evaporation from individual atmometers was measured and recorded 90 minutes after treatment was imposed. Results are shown in Table 2.

The effect of treatment is expressed in the following manner: treatment evaporation (ml)/control evaporation (ml)=% of control=Evaporation Suppressing Ability (ESA).

TABLE 2

| Treatment | Amount Applied | ESA (% of control) |
|---|---|---|
| Lotion I | 2.54 g | 66.11 ± 9.59 |
| Skin Cream I | 1.68 g | 82.2 ± 22.6 |
| Skin Cream II | 10.41 g | 25.9 ± 2.79 |

The results indicate all treatments inhibited water loss from atmometers.

Example 4

An Oil/Water Lotion Containing *Lycopersicon pennellii* Natural Plant Extract

| SKIN LOTION I | |
|---|---|
| Raw Materials | % by weight |
| 1. Mineral Oil | 19.0 |
| 2. Tween 60 surfactant* | 7.5 |
| 3. Water | 65.0 |
| 4. *L. pennellii* Natural Plant Extract (TE) | 8.5 |
| | 100.0 |

*"Tween 60" is the trademark for polysorbate 60 polyoxyethylene 20 sorbitan monostearate as produced by ICI Americas Co., Wilmington, Delaware 19897.

FORMULATION NOTE: Add preservative, as required.

Key Properties: A basic oil-in-water emulsion-type lotion which has a pleasant whitish appearance and a pleasant soft feel.

The composition of Example 4 is a modification of an oil-in-water mineral oil lotion included in Flick, *Cosmetic and Toiletry Formulations* (1984) at page 352.

Example 5

An Emollient Lotion Containing *Lycopersicon pennellii* Natural Plant Extract

| SKIN LOTION II | |
|---|---|
| Raw Materials | % by weight |
| 1. Tween 60 surfactant* | 7.5 |
| 2. Water | 65.0 |
| 3. *L. pennellii* Natural Plant Extract (TE) | 27.5 |
| | 100.0 |

*"Tween 60" is the trademark for polysorbate 60 polyoxyethylene 20 sorbitan monostearate as produced by ICI Americas Co., Wilmington, Delaware 19897.

Key Properties: A basic emulsion-type lotion which is tan in color, and soft and oily (although slightly sticky) on the skin.

Example 6

An Emollient Cream I Containing *Lycopersicon pennellii* Natural Plant Extract

| SKIN CREAM I | |
|---|---|
| Raw Materials | % by weight |
| 1. Cottonseed Oil | 15.0 |
| 2. Tween 60 surfactant* | 2.0 |
| 3. Water | 68.0 |
| 4. Sorbitol Solution, 70% | 6.0 |

-continued
SKIN CREAM I

| Raw Materials | % by weight |
| --- | --- |
| 5. *L. pennellii* Natural Plant Extract (TE) | 9.0 |
| | 100.0 |

*"Tween 60" is the trademark for polysorbate 60 polyoxyethylene 20 sorbitan monostearate as produced by ICI Americas Co., Wilmington, Delaware 19897.

Key Properties: A basic emollient cream that stays completely in emulsion, has a pleasant eggshell color, and has a pleasant, soft feel to the skin.

The composition of Example 6 is a modification of an emollient cream composition included in Flick, *Cosmetic and Toiletry Formulations* (1984) at page 160.

Example 7

An Emollient Cream II Containing *Lycopersicon pennellii* Natural Plant Extract

SKIN CREAM II

| Raw Materials | % by weight |
| --- | --- |
| 1. Tween 60 surfactant* | 6.0 |
| 2. Water | 68.0 |
| 3. *L. pennellii* Natural Plant Extract (TE) | 20.0 |
| 4. Sorbitol solution, 70% | 6.0 |
| | 100.0 |

*"Tween 60" is the trademark for polysorbate 60 polyoxyethylene 20 sorbitan monostearate as produced by ICI Americas Co., Wilmington, Delaware 19897.

Key Properties: An oil-less cream emollient which is tan in color, stays completely in solution, and is soft and oily (although slightly sticky) to the skin.

The composition of Example 7 is a modification of a cream-emollient composition included in Flick, *Cosmetic and Toiletry Formulations* (1984) at page 160.

Example 8

Baby Lotion Containing *Lycopersicon pennellii* Natural Plant Extract

BABY LOTION I

| Raw Materials | % by weight |
| --- | --- |
| 1. Imwitor 960K Glyceride* | 8.0 |
| 2. Miglyol 812 Neutral Oil** | 5.0 |
| 3. *L. pennellii* Natural Plant Extract (TE) | 5.0 |
| 4. Glycerine | 5.0 |
| 5. Water (Distilled) | 77.0 |
| | 100.0 |

*"Imwitor 960K Glyceride" is the trademark for glyceryl stearates s.e. CTFA as produced by Kay-Fries, Inc., Montvale, NJ 07645.
**"Miglyol 812 Neutral Oil" is the trademark for caprylic/capric triglyceride CTFA as produced by Kay-Fries, Inc., Montvale, NJ 07645.

Formulation Note: Add preservative, as required.

The composition of Example 8 is a modification of a glyceride/oil/glycerine baby lotion composition included in Flick, *Cosmetic and Toiletry Formulations* (1984) at page 35.

Example 9

Baby Cream Containing *Lycopersicon pennellii* Natural Plant Extract

BABY CREAM I

| Raw Materials | % by weight |
| --- | --- |
| 1. *L. pennellii* Natural Plant Extract (TE) | 3.0 |
| 2. Sorbo Sorbitol Solution* | 27.0 |

-continued
BABY CREAM I

| Raw Materials | % by weight |
| --- | --- |
| 3. Mineral Oil | 10.0 |
| 4. Beeswax | 1.0 |
| 5. Ceresin Wax | 1.0 |
| 6. Zinc Oxide (USP) | 20.0 |
| 7. Water | 38.0 |
| | 100.0 |

*"Sorbo Sorbitol Solution" is the trademark for sorbitol solution (USP), 70% in water as produced by ICI Americas, Inc., Wilmington, Delaware 19897.

Key Properties: May be modified to include Vitamin A, Vitamin D, antihistamines, analgesics, cod liver oil or Peru Balsam to provide a diaper rash treatment; exceptionally stable and spreads well on the skin.

The composition of Example 9 is a modification of a sorbitol/zinc oxide baby cream composition included in Flick, *Cosmetic and Toiletry Formulations* (1984) at page 34.

Example 10

Antiperspirant Cream Containing *Lycopersicon pennellii* Natural Plant Extract.

ANTIPERSPIRANT CREAM I

| Raw Materials | % by weight |
| --- | --- |
| 1. Cetyl alcohol | 5.0 |
| 2. *L. pennellii* Natural Plant Extract (TE) | 9.0 |
| 3. Water | 46.0 |
| 4. Aluminum Chlorhydroxide (50% in water) | 40.0 |
| | 100.0 |

The composition of Example 10 is a modification of a chlorhydroxide/alcohol antiperspirant cream composition included in Flick, *Cosmetic and Toiletry Formulations* (1984) at page 3.

Example 11

Aerosol Antiperspirant Containing *Lycopersicon pennellii* Natural Plant Extract

ANTIPERSPIRANT-AEROSOL I

| Raw Materials | % by weight |
| --- | --- |
| 1. Stearic Acid (Triple Pressed) | 8.0 |
| 2. Cetyl Alcohol | 1.2 |
| 3. *L. pennellii* Natural Plant Extract (TE) | 3.0 |
| 4. Propylene Glycol | 4.0 |
| 5. Water | 43.8 |
| 6. Aluminum chlorhydroxide (50% solution in water) | 40.0 |
| | 100.0 |

The composition of Example 11 is a modification of a chlorhydroxide aerosol antiperspirant composition included in Flick, *Cosmetic and Toiletry Formulations* (1984) at page 2.

Example 12

Baby Shampoo Containing *Lycopersicon pennellii* Natural Plant Extract

BABY SHAMPOO I

| Raw Materials | % by weight |
| --- | --- |
| 1. Miranol 2MCA Modified Surface Active Agent* | 15.0 |
| 2. Tween 20 Surfactant** | 13.5 |
| 3. *L. pennellii* Natural Plant Extract (TE) | 1.5 |

-continued
BABY SHAMPOO I

| Raw Materials | % by weight |
|---|---|
| 4. Water | 70.0 |
| | 100.0 |

*"Miranol 2MCA Modified Surface Active Agent" is the trademark for amphoteric salt, coconut and lauric fatty radicals, hydrophilics as produced by Miranol Chemical Co., Inc., South Brunswick, New Jersey 08810.
**"Tween 20 Surfactant" is the trademark for polysorbate 20 polyoxyethylene 20 sorbitan monolaurate as produced by ICI Americas Co., Wilmington, Delaware 19897.

The composition of Example 12 is a modification of a baby shampoo composition included in Flick, *Cosmetic and Toiletry Formulations* (1984) at page 45.

Example 13

Bath Oil Containing *Lycopersicon pennellii* Natural Plant Extract

BABY OIL I

| Raw Materials | % by weight |
|---|---|
| 1. Miglyol 812 Neutral Oil* | 80.0 |
| 2. *L. pennellii* Natural Plant Extract (TE) | 14.0 |
| 3. Perfume | 6.0 |
| | 100.0 |

*"Miglyol 812 Neutral Oil" is the trademark for caprylic/capric triglyceride CTFA as produced by Kay-Fries, Inc., Montvale, NJ 07645.

The composition of Example 13 is a modification of a bath oil composition included in Flick, *Cosmetic and Toiletry Formulations* (1984) at page 45.

Example 14

Hair Dressing Containing *Lycopersicon pennellii* Natural Plant Extract.

HAIR DRESSING I

| Raw Materials | % by weight |
|---|---|
| 1. Petrolatum | 15.0 |
| 2. Mineral Oil | 10.0 |
| 3. Lanolin | 20.0 |
| 4. Beeswax | 12.0 |
| 5. *L. pennellii* Natural Plant Extract (TE) | 5.0 |
| 6. Tween 60 Surfactant* | 5.0 |
| 7. Borax | 1.0 |
| 8. Water | 32.0 |
| | 100.0 |

*"Tween 60" is the trademark for polysorbate 60 polyoxyethylene 20 sorbitan monostearate as produced by ICI Americas Co., Wilmington, Delaware 19897.

Formulation Note: Add preservative, as required.

The composition of Example 14 is a modification of a hair dressing composition included in Flick, *Cosmetic and Toiletry Formulations* (1984) at page 271.

Example 15

After shave Lotion Containing *Lycopersicon pennellii* Natural Plant Extract.

AFTER SHAVE LOTION I

| Raw Materials | % by weight |
|---|---|
| 1. SDA-40 Alcohol | 76.0 |
| 2. Water | 23.0 |
| 3. *L. pennellii* Natural Plant Extract (TE) | 1.0 |
| | 100.0 |

Formulation Note: Add perfume, as required.

The composition of Example 15 is a modification of an alcohol/water after shave lotion composition included in Flick, *Cosmetic and Toiletry Formulations* (1984) at page 478.

Example 16

Shave Cream Containing *Lycopersicon pennellii* Natural Plant Extract.

SHAVE CREAM I

| Raw Materials | % by weight |
|---|---|
| 1. Glycolipid fraction of (G) *L. pennellii* Natural Plant Extract | 10.0 |
| 2. Sorbitol (70%) | 10.0 |
| 3. Water (purified) | 70.8 |
| 4. Triethanolamine | 4.6 |
| 5. Water (purified) | 4.6 |
| | 100.0 |

Formulation Note: Add antimicrobial (water-soluble) and/or perfume, as needed.

The composition of Example 16 is a modification of a sorbitol/fatty acids shave cream composition included in Flick, *Cosmetic and Toiletry Formulations* (1984) at page 493.

Example 17

Bar Soap Containing *Lycopersicon pennellii* Natural Plant Extract.

BAR SOAP I

| Raw Materials | % by weight |
|---|---|
| 1. Igepon AC-78 Surfactant* | 25.0 |
| 2. Milled Bleached White Flour | 52.5 |
| 3. Glycerine | 3.0 |
| 4. Cornstarch | 4.0 |
| 5. *L. pennellii* Natural Plant Extract (TE) | 1.0 |
| 6. Isopropyl Myristate | 2.0 |
| 7. Lactic Acid | 2.0 |
| 8. Water | 10.5 |
| | 100.0 |

*"Igepon AC-78 Surfactant" is the trademark for coconut acid ester of sodium isethionate (83% active) as produced by GAF Corp., New York, New York.

The composition of Example 17 is a modification of an bar soap composition included in Flick, *Cosmetic and Toiletry Formulations* (1984) at page 506.

Example 18

Sunscreen Cream Containing *Lycopersicon pennellii* Natural Plant Extract.

SUNSCREEN CREAM I

| Raw Materials | % by weight |
|---|---|
| 1. Amerscreen P U.V. Absorber* | 3.0 |
| 2. Stearic Acid | 2.7 |
| 3. Amerlate P Isopropyl Ester** | 6.0 |
| 4. Cetyl Alcohol | 3.0 |
| 5. Isopropyl Myristate | 7.5 |
| 6. Glyceryl Stearate | 4.0 |
| 7. *L. pennellii* Natural Plant Extract (TE) | 5.0 |
| 8. Water | 64.5 |
| 9. Triethanolamine | 1.3 |
| 10. Glucam E-20 Glucose Derivative*** | 3.0 |

-continued
SUNSCREEN CREAM I
| Raw Materials | % by weight |
|---|---|
| | 100.0 |

*"Amerscreen P U.V. Absorber" is the trademark for ethyl dihydroxypropyl PABA U.V. absorber, propoxylated (2 moles) ethyl paraaminobenzoate as produced by Amerchol Unit, CPC International, Inc., Edison, New Jersey 08817.
**"Amerlate P Isopropyl Ester" is the trademark for isopropyl lanolate used as wetting agent as produced by Amerchol Unit, CPC International, Inc., Edison, New Jersey 08817.
****"Glucam E-20 Glucose Derivative" is the trademark for methyl gluceth-20, ethoxylated (20 moles) as produced by Amerchol Unit, CPC International, Inc., Edison, New Jersey 08817.

Formulation Note: Add perfume and/or preservative, as required.

The composition of Example 18 is a modification of a sunscreen cream composition included in Flick, *Cosmetic and Toiletry Formulations* (1984) at page 520.

Example 19

Baby Cream Containing *Lycopersicon pennellii* Bitter Glycolipid Fraction.

BABY CREAM I
| Raw Materials | % by weight |
|---|---|
| 1. *L. pennellii* Bitter Glycolipid Fraction (BG) | 3.0 |
| 2. Sorbo Sorbitol Solution* | 27.0 |
| 3. Mineral Oil | 10.0 |
| 4. Beeswax | 1.0 |
| 5. Ceresin Wax | 1.0 |
| 6. Zinc Oxide (USP) | 20.0 |
| 7. Water | 38.0 |
| | 100.0 |

*"Sorbo Sorbitol Solution" is the trademark for sorbitol solution (USP), 70% in water as produced by ICI Americas, Inc., Wilmington, Delaware 19897.

Key Properties: May be modified to include Vitamin A, Vitamin D, antihistamines, analgesics, cod liver oil or Peru Balsam to provide a diaper rash treatment; exceptionally stable and spreads well on the skin.

The composition of Example 19 is a modification of a sorbitol/zinc oxide baby cream composition included in Flick, *Cosmetic and Toiletry Formulations* (1984) at page 34.

Example 20

Nail Polish Containing Bitter Glycolipid Fraction of *Lycopersicon pennellii* Natural Plant Extract.

NON-NAIL BITING NAIL POLISH
| Raw Materials | % by weight |
|---|---|
| 1. Nail Polish (colored or colorless) | 98. |
| 2. *Lycopersicon pennillii* Glycolipid Fraction (BG) | 2. |
| | 100.0 |

Example 21

Lip Balm Containing Non-bitter Glucolipid Fraction of *Lycopersicon pennellii* Natural Plant Extract.

LIP BALM I
| Raw Materials | % by weight |
|---|---|
| 1. Hoechst Wax S* | 13.0 |
| 2. Hydrogenated Castor Wax | 7.0 |
| 3. Protopet Petrolatum | 10.0 |
| 4. Carnation White Mineral Oil | 50.0 |
| 5. Non-bitter Glucolipid fraction (NBG) of | 20.0 |

LIP BALM I (continued)
| Raw Materials | % by weight |
|---|---|
| *L. pennellii* Natural Plant Extract | 100.0 |

*"Hoechst Wax S" is the trademark for acid wax derived from montan wax as produced by American Hoechst Corp., Chemicals Division, Somerville, New Jersey 08876, Montvale, NJ 07645.

The composition of Example 21 is a modification of a chap stick composition included in Flick, *Cosmetic and Toiletry Formulations* (1984) at page 82.

Example 22

Lipstick Containing Non-bitter Glucolipid Fraction of *Lycopersicon pennellii* Natural Plant Extract.

LIPSTICK I
| Raw Materials | % by weight |
|---|---|
| 1. Candelilla wax | 11.5 |
| 2. Beeswax | 15.0 |
| 3. Amerlate P Isopropyl Ester* | 15.0 |
| 4. Adol 66 Fatty Alcohol** | 14.0 |
| 5. Non-bitter Glucolipid fraction (NBG) of *L. pennellii* Natural Plant Extract | 7.0 |
| 6. Pigment | 37.5 |
| | 100.0 |

*"Amerlate P Isopropyl Ester" is the trademark for isopropyl lanolate used as wetting agent as produced by Amerchol Unit CPC International, Inc., Edison, New Jersey 08817.
**"Adol 66 Fatty Alcohol" is the trademark for cosmetic isostearyl alcohol, hydroxyl value 180–200 as produced by Ashland Chemical Co., Columbus, Ohio 43216.

The composition of Example 22 is a modification of a lipstick composition included in Flick, *Cosmetic and Toiletry Formulations* (1984) at page 115.

Example 23

Margarine-Like Spread Containing Lycopersicon pennellii Non-bitter Glucolipid (NBG) Fraction The non-bitter glucolipid (NBG) fraction can be used as a partial replacement for the fat in margarine by mixing (by weight) 1 part NBG fraction with 3 parts margarine, followed by whipping to the desired texture. The resultant margarine has the taste and characteristics of regular margarine, i.e., creamy texture, ability to pan fry, ability to melt on toast, etc.

Example 24

Pancakes Made With Lycopersicon pennellii Non-bitter Glucolipid (NBG) Fraction

Pancakes were prepared from a dry pancake mix which called for the addition of about a tablespoon of liquid shortening per cup of dry mix prior to, or along with the addition of the liquid when preparing the pancake batter. A pancake batter was prepared in accordance with a recipe except that NBG fraction was used in place of the customary shortening. The pancakes were cooked on a griddle using NBG fraction as a greasing agent. The pancakes were eaten, and their flavor and texture were judged by a panel of tasters as being the same as those of pancakes prepared in a similar manner using ordinary shortening.

Example 25

Salad Dressing Made With Lycopersicon pennellii Non-bitter Glucolipide (NBG) Fraction Place in a blender container:

½ cup vinegar
1½ cup NBG fraction
1 tsp salt
¼ tsp peppercorns
½ tsp dry mustard Cover the container and blend for about 20 seconds at high speed. Pour the blended dressing into a jar, cover and store in the refrigerator.

A panel of tasters judged that the resultant salad dressing has the taste and texture of a salad dressing made with a conventional salad oil.

TABLE I

PROCESS FOR THE PURIFICATION AND SEPARATION OF NON-BITTER AND BITTER GLUCOLIPID

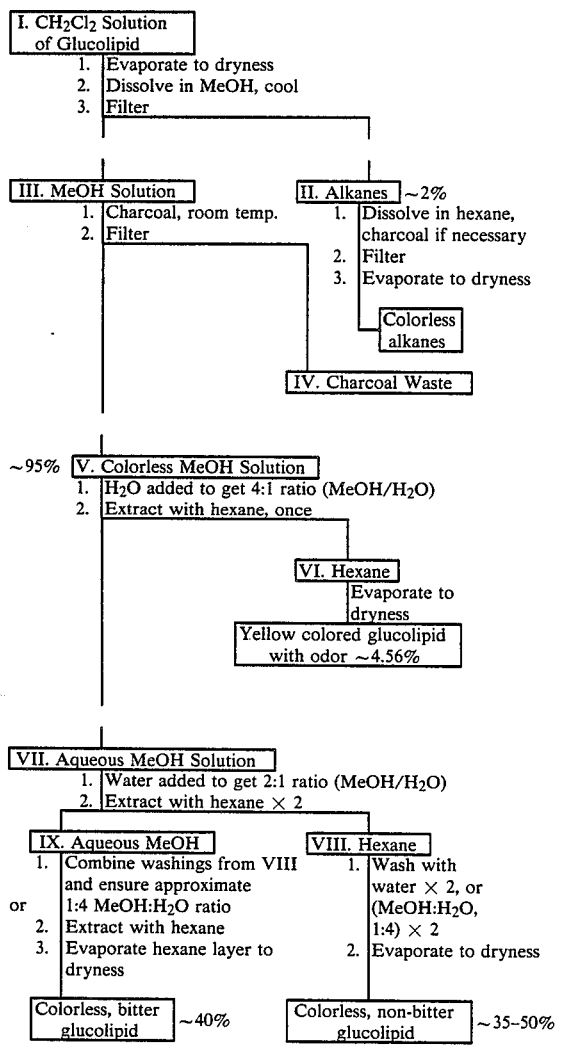

SUMMARY

Thus it can be seen that the present invention comprises a new class of 2,3,4-tri-0-acylhexoses and mixtures thereof. These new hexoses can be synthesized using known chemical methods. Alternatively, the new compounds, and especially mixtures thereof, are obtained as the result of selective extraction and purification of the epicuticular exudate from *Lycopersicon pennellii* plant parts. Mixtures of 2,3,4-tri-0-acylhexoses, especially as found in the *Lycopersicon pennellii* natural plant extract (TE) fractions thereof, are useful as evaporation suppressants, antitranspirants, and antidesiccants.

The *Lycopersicon pennellii* natural plant extract is also useful in making new cosmetic and toiletry formulations. In the new cosmetic and toiletry formulations, the *Lycopersicon pennellii* natural plant extract can serve as an emulsifier, an emollient, a moisturizer, a surfactant, a thickening agent, and a preservative, as well as a source of fragrance and color. Since the *Lycopersicon pennellii* glycolipid-containing natural plant extract is non-irritating to the eye and skin, *Lycopersicon pennellii* natural plant extract is especially useful as an ingredient in cosmetics and toiletries to be used for babies and hypersensitive adults.

The non-bitter glucolipids (NBG) can be used in cosmetic compositions where taste is of some concern, e.g., in lipsticks. The bitter glucolipids (BG) can be used when taste is of no concern, or where the bitter taste is advantageous to discourage ingestion of the product that contains it.

The *Lycopersicon pennellii* G fraction, and especially the NBG subfraction thereof, is useful as a low calorie fat substitute in foods. The G fraction is only partially hydrolyzed by pancreatic lipase; therefore fewer fatty acids are in a form available for the body to metabolize. Fewer available fatty acids effectively means fewer calories. Both the G and NBG fractions are colorless, oily liquids at room temperature; thus both the G and NBG fractions have the physical characteristics of many conventional cooking oils. As a result both the G and NBG fractions can be used as a fat substitute in almost any food. In addition both the G and NBG fractions can be used for frying, thus making conventional fried foods lower in calories.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. 2,3,4-tri-0-acyl D- and/or L-hexoses having the structure:

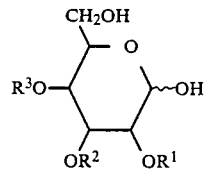

wherein
the hexose is a hexose selected from the group consisting of glucose, mannose, galactose, allose, altrose, gulose, idose, and talose,
the anomeric (C-1) substituent is either alpha or beta, and
$R^1$, $R^2$, and $R^3$ are fatty acids independently selected from the group consisting of normal-, iso-, and anteiso- alkanoic and alkenoic acids containing 3 to 30 carbons.

2. The compound of claim 1 wherein said fatty acids contain 4 to 20 carbons.

3. The compound of claim 1 wherein said hexose is glucose.

4. The compound of claim 1 wherein said hexose is a D-hexose.

5. The compound of claim 1 wherein at least one of $R^1$, $R^2$, and $R^3$ is a fatty acid containing more than 7 carbons.

6. The compound of claim 1 wherein at least one of $R^1$, $R^2$, and $R^3$ is a fatty acid containing 10 to 30 carbons.

7. The compound of claim 1 wherein at least one of $R^1$, $R^2$, and $R^3$ is a fatty acid containing 10 to 18 carbons.

8. The compound of claim 7 wherein said hexose is glucose.

9. The compound of claim 8 wherein said glucose is a D-glucose.

10. The compound of claim 1 wherein $R^1$, $R^2$, and $R^3$ are each fatty acids containing 3 to 7 carbon atoms.

11. A mixture of non-bitter 2,3,4-tri-0-acyl D- and/or L-hexoses having the structure:

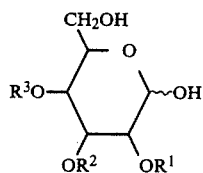

wherein
the hexose is a hexose selected from the group consisting of glucose, mannose, galactose, allose, altrose, gulose, idose, and talose,
the anomeric (C-1) substituent is either alpha or beta,
$R^1$, $R^2$, and $R^3$ are fatty acids independently selected from the group consisting of normal-, iso-, and anteiso- alkanoic and alkenoic acids containing 3 to 30 carbons, provided that at least one of $R^1$, $R^2$, or $R^3$ is a fatty acid containing more than 7 carbons.

12. A total extract mixture consisting essentially of recovered products from selective organic extraction of the epicuticular exudate from *Lycopersicon pennellii* plant parts, said total extract consisting essentially of 88–95% glucolipids, 5–10% alkanes and 1% terpenoids.

13. The bitter glucolipid (BG) fraction of *Lycopersicon pennellii* epicuticular exudate extract recovered by selective extraction.

14. The non-bitter glucolipid (NBG) fraction of *Lycopersicon pennellii* exudate extract recovered by selective extraction.

15. A composition for use as an antitranspirant, antidesiccant or evaporation suppressant which composition contains, as active ingredient, a mixture which is the same as the epicuticular exudate extract or a glucolipid-containing fraction thereof obtained from selective organic extraction of *Lycopersicon pennellii*.

16. The composition of claim 15 wherein the extract is the total extract.

17. The composition of claim 15 wherein the extract is the glucolipid fraction.

18. The composition of claim 15 wherein the extract is the non-bitter glucolipid subfraction.

19. The composition of claim 15 wherein the extract is the bitter glucolipid subfraction.

20. A cosmetic composition for application to the external surface of skin or hair comprising an active agent homogenized with carriers, diluents and/or additives conventionally applied in the preparation of cosmetics, characterized in that it contains as active agent a mixture which is the same as the epicuticular exudate extract or glucolipid-containing fraction thereof recovered from selective organic extraction *Lycopersicon pennellii*.

21. The composition of claim 20 wherein the extract is the total extract.

22. The composition of claim 20 wherein the extract is the glucolipid fraction.

23. The composition of claim 20 wherein the extract is the non-bitter glucolipid subfraction.

24. The composition of claim 20 wherein the extract is the bitter glucolipid subfraction.

25. An edible composition for use as a food which contains the non-bitter glucolipid subfraction of epicuticular exudate extract receved from selective extraction of *Lycopersicon pennellii*, in admixture with additional ingredients conventionally used in foodstuffs.

26. A method to prepare a food composition of low calorie content which comprises substituting for all or a part of the fat component of a foodstuff a corresponding amount of the non-bitter glucolipid subfraction of *Lycopersicon pennellii* epicuticular exudate extract.

27. A method to obtain a glucolipid-containing extract from *Lycopersicon pennellii* which comprises:
(a) briefly exposing *Lycopersicon pennellii* plant parts to an organic solvent;
(b) recovering the resulting mixture of organic solvent and dissolved *Lycopersicon pennellii* epicuticular exudate extract; and
(c) removing the organic solvent from said *Lycopersicon pennellii* epicuticular exudate extract to obtain a total extract containing glucolipid.

28. The method of claim 27 which further includes:
(a) redissolving the total extract in methanol to obtain a methanol solution;
(b) cooling said methanol solution to effect the crystallization of alkanes present in the total extract to obtain a solid and a supernatant;
(c) recovering the supernatant from step (b);
(d) decolorizing the supernatant to obtain a decolorized glucolipid-containing solution; and
(e) removing the solvent from the glucolipid-containing solution to recover a glucolipid fraction.

29. The method of claim 28 which further includes separating the glucolipid fraction into bitter and non-bitter fractions.

30. The method of claim 29 which comprises extracting a methanol:$H_2O$ 2:1 solution of the glucolipid fraction with hexane.

31. A method to obtain bitter and non-bitter glucolipid fractions which comprises:
(1) stirring the glucolipid fraction produced according to the method of claim 28 with the mixture of methanol and water, said mixture being at a ratio of approximately 4:, MeOH:$H_2O$;
(2) extracting the mixture from step 1 with hexane;
(3) evaporating said hexane from the solution of step 2 to yield colored glucolipid;
(4) diluting said MeOH:$H_2O$/glucolipid from step 3 with water to form a mixture having a ratio of approximately 2:1, MeOH:$H_2O$;
(5) extracting said mixed MeOU:$H_2O$/glucolipid solution from step 4 at least twice with hexane;
(6) separating the hexane from the washed MeOH:$H_2O$/glucolipid;
(7) washing the hexane resulting from step 6 with water;

(8) evaporating the hexane and the water from the solution of step 7 to yield colorless, non-bitter *Lycopersicon pennellii* glucolipid;

(9) combining the washings from steps 4 and 5;

(10) extracting said combined washings from steps 4 and 5 with hexane;

(11) evaporating the hexane from said combined washings of step 10 to yield colorless, bitter *Lycopersicon pennellii* glucolipid.

32. A method to obtain a glucolipid-containing extract from *Lycopersicon pennellii* comprising:

(a) briefly exposing *Lycopersicon pennellii* plant parts to organic solvent and recovering and epicuticular exudate extract, and (b) separating alkanes and pigments from said extract and recovering a purified glucolipid fraction.

33. The method of claim 32 which further includes separation of said glucolipid fraction into a bitter glucolipid subfraction and a non-bitter glucolipid subfraction.

34. *Lycopersicon pennellii* non-bitter glucolipid produced according to the method of claim 31, 33, 29 or 30.

35. *Lycopersicon pennellii* bitter glucolipid produced according to the method of claim 31, 33, 29 or 30.

* * * * *